US012790639B2

(12) United States Patent
Euro et al.

(10) Patent No.: US 12,790,639 B2
(45) Date of Patent: *Nov. 10, 2026

(54) METHOD FOR DETERMINING AMOUNTS OF NAD METABOLITES FROM SAMPLE AND METHODS AND USES RELATED THERETO

(71) Applicant: HELSINGIN YLIOPISTO, Helsinki (FI)

(72) Inventors: Liliya Euro, Helsinki (FI); Anu Wartiovaara, Helsinki (FI)

(73) Assignee: NADMED OY, Helsinki (FI)

( * ) Notice: Subject to any disclaimer, the term of this patent is extended or adjusted under 35 U.S.C. 154(b) by 0 days.

This patent is subject to a terminal disclaimer.

(21) Appl. No.: 19/037,543

(22) Filed: Jan. 27, 2025

(65) Prior Publication Data

US 2025/0207172 A1 Jun. 26, 2025

Related U.S. Application Data

(63) Continuation of application No. 18/004,790, filed as application No. PCT/FI2021/050529 on Jul. 7, 2021.

(30) Foreign Application Priority Data

Jul. 9, 2020 (FI) ..................................... 20205738

(51) Int. Cl.

*G01N 31/00* (2006.01)
*C12Q 1/32* (2006.01)
*G01N 33/52* (2006.01)
*G01N 33/53* (2006.01)
*G01N 33/575* (2026.01)

(52) U.S. Cl.

CPC ............... *C12Q 1/32* (2013.01); *G01N 33/52* (2013.01); *G01N 33/575* (2026.01); *G01N 2800/28* (2013.01)

(58) Field of Classification Search

None

See application file for complete search history.

(56) References Cited

U.S. PATENT DOCUMENTS 4,556,634 A 12/1985 Misaki et al.
6,287,796 B1 9/2001 Jacobson et al.
2023/0257795 A1 8/2023 Euro et al.

FOREIGN PATENT DOCUMENTS

EP 0322591 A2 7/1989
WO 88/08882 A1 11/1988
WO WO-2015145387 A1 * 10/2015 ............ G16B 50/30
WO 2018/002215 A1 1/2018

OTHER PUBLICATIONS

Lazzarino et al. Analytical Biochemistry, 322 (2003) pp. 51-59. (Year: 2003).*

Gonzalez et al. (Yeast, Vo.13, pp. 1347-1355, 1997). (Year: 1997).*

Gowda et al. Anal. Chem. Apr. 18, 2017; 89(8): 4620-4627. (Year: 2017).*

Gonzalez et al. (Yeast, vol. 14, pp. 1347-1355; 1997) (Year: 1997).*

Sellick et al. Metabolmics, May 18, 2010; vol. 6, pp. 427-438 (Year: 2010).*

International Search Report and Written Opinion for corresponding Application No. PCT/FI2021/050529 (mailed Dec. 10, 2021).

Sellick et al., "Evaluation of Extraction Processes for Intracellular Metabolite Profiling of Mammalian Cells: Matching Extraction Approaches to Cell Type and Metabolite Targets," Metabolomics 6(3):427-438 (2010).

Umemura et al., "Determination of Oxidized and Reduced Nicotinamide Adenine Dinucleotide in Cell Monolayers Using a Single Extraction Procedure and a Spectrophotometric Assay," Anal. Biochem. 338(1):131-135 (2005).

Gonzalez et al., "A Rapid and Reliable Method for Metabolite Extraction in Yeast Using Boiling Buffered Ethanol," 13(14):1347-1355 (1997).

Campbell et al., "Development and Validation of a Robust Specific Enzyme Mediated Assay for Phenylalanine in Serum," Clinica Chimica Acta 210(3):197-210 (1992).

Park et al., "Metabolic Profiling of: Evaluation of Methods for Extraction of Intracellular metabolites Using UPLC/Q-TOF-MS," App. Biochem. Biotechnol. 167(3):425-438 (2012).

Lilius et al., "Quantitative Extraction and Estimation of Intracellular Nicotinamide Nucleotides of *Escherichia coli*," Anal. Biochem. 99(1):22-27 (1979).

Pirinen et al., "Niacin Cures Systemic NAO+ Deficiency and Improves Muscle Performance in Adult-Onset Mitochondrial Myopathy," Cell Metabolism 31(6):1078-1090 (2020).

Zerez et al., "Spectrophotometric Determination of Oxidized and Reduced Pyridine Nucleotides in Erythrocytes Using a Single Extraction Procedure," Analytical Biochemistry 164(2):367-373 (1987).

Paglia et al., "Intracellular Metabolite Profiling of Platelets: Evaluation of Extraction Processes and Chromatographic Strategies," Journal of Chromatography B 898:111-120 (2012).

(Continued)

*Primary Examiner* — Lisa V Cook

(74) *Attorney, Agent, or Firm* — Troutman Pepper Locke LLP (Rochester)

(57) ABSTRACT

The present invention relates to the fields of life sciences and medicine. Specifically, the invention relates to methods and kits for preparing an extract comprising metabolites such as NAD+, NADP+, NADH and NADPH from a sample of a subject and to a method for determining amounts of NAD+, NADP+, NADH, NADPH, NAD+/NADH ratio, NADPH/NADP+ ratio, NAD pool, and/or NADP pool from a sample obtained from a subject. The present invention also relates to an extract comprising metabolites such as NAD+, NADP+, NADH and NADPH. The methods and kits can be used for diagnostics purposes or for monitoring changes in health status of a person. Furthermore, the present invention relates to a method and kit for determining disorders of a subject.

9 Claims, 12 Drawing Sheets

(56) References Cited

OTHER PUBLICATIONS

Shryock et al., "Extraction of Adenine Nucleotides From Cultured Endothelial Cells," Analytical Biochemistry 159(1):73-81 (1985).
Williams and Hill, "The 4 D's of Pellagra and Progress," Int J of Tryptophan Res 13:1-12 (2020).
Szal et al., "Changes in Energy Status of Leaf Cells as a Consequence of Mitochondrial Genome Rearrangement," Planta 227:697-706 (2008).

* cited by examiner

METHOD FOR DETERMINING AMOUNTS OF NAD METABOLITES FROM SAMPLE AND METHODS AND USES RELATED THERETO

This application is a continuation of U.S. patent application Ser. No. 18/004,790, which is a national stage application under 35 U.S.C. § 371 of International Application No. PCT/FI2021/050529, filed Jul. 7, 2021, which claims priority benefit to Finland Application No. 20205738, filed Jul. 9, 2020.

FIELD OF THE INVENTION

The present invention relates to the fields of life sciences and medicine. Specifically, the invention relates to a method for preparing an extract comprising metabolites such as NAD+, NADP+, NADH and NADPH from a sample of a subject and to a method for determining NAD+, NADP+, NADH, NADPH, NAD+/NADH ratio, NADPH/NADP+ ratio, NAD pool (NAD+ and NADH together), and/or NADP pool (NADP+ and NADPH together) from a sample obtained from a subject. The present invention also relates to an extract comprising metabolites such as NAD+, NADP+, NADH and NADPH. Also, the present invention relates to a kit comprising an extraction solution, a detection system comprising an electron carrier, chromogen and non-ionic detergent for determining NAD+, NADP+, NADH, NADPH, NAD+/NADH ratio, NADPH/NADP+ ratio, NAD pool (NAD+ and NADH together), and/or NADP pool (NADP+ and NADPH together), and optionally GSH, GSSG and/or GSH/GSSG ratio, from a sample of a subject. Still, the present invention relates to use of the kit of the present invention for determining NAD+, NADP+, NADH, NADPH, NAD+/NADH ratio, NADPH/NADP+ ratio, NAD pool (NAD+ and NADH together), NADP pool (NADP+ and NADPH together), GSH, GSSG and/or GSH/GSSG ratio or changes thereof in a sample of a subject e.g. for diagnostics purposes or for monitoring changes in health status of a person. Furthermore, the present invention relates to a method and kit for determining disorders of a subject.

BACKGROUND OF THE INVENTION

Vitamin B3 plays a key role in maintenance of homeostasis of all tissues. Both a lack and an excessive amount of vitamin B3 are detrimental to health and vitamin B3 is associated with many serious diseases (Williams A C and Hill L J, 2020 Int J Tryptophan Res). Humans need vitamin B3 to produce four NAD metabolites which are also called pyridine nucleotides. The NAD metabolites consist of oxidized forms NAD+ and NADP+; and reduced forms NADH and NADPH. They function in pairs, and individual concentrations of NAD+, NADP+, NADH, NADPH and as well as their ratios (NAD+/NADH and NADPH/NADP+) regulate a number of vital metabolic processes such as gene expression, cell energy metabolism, reductive biosynthesis, defense against oxidative stress and calcium signaling. Therefore, analysis of the individual concentrations and the ratios are essential to make conclusion on B3/NAD homeostasis. Sufficiency of vitamin B3 can be assessed by measurement of NAD pool (NAD+ plus NADH metabolites) and NADP pool (NADP+ plus NADPH metabolites). Moreover, levels of NADP+ and NADPH and their ratio NADPH/NADP+ directly regulate levels of reduced glutathione in the cells. Glutathione plays a critical role in protecting cells from oxidative damage and maintaining the redox homeostasis and its metabolism has been well studied. Reduced glutathione is an antioxidant, once it is oxidized it can be recycled back to its reduced form using NADPH metabolite. Therefore, analysis of NAD- and glutathione forms from biological samples give an excellent view of cellular reduced-oxidized (redox) state. Assays that would allow analysis of all these forms from a single biological sample have not been available, as the forms have required specific extraction methods and analysis platforms.

Concentrations of NAD+ and NADP+ in a biological sample can be measured using LC-MS, whereas their pool NAD+ plus NADP+ can be measured using HPLC. LC-MS and HPLC are expensive, require special expertise, and are not readily available in every laboratory. Compared to the oxidized NAD forms reduced NAD forms are much more difficult to isolate and analyze, due to their special requirements for stability.

For example, U.S. Pat. No. 6,287,796 B1 describes a colorimetric method and kits for measuring intracellular concentrations of NAD metabolites in a biological sample. The patent describes a method for measuring total pools of NAD (NAD+ and NADH together) and NADP (NADP+ and NADPH together) to calculate the so called niacin number ((NAD/NADP)*100) showing sufficiency of vitamin B3 supplementation. The method does not allow separate analysis of the reduced forms (NADH or NADPH) and the oxidized forms (NAD+ or NADP+) of NAD metabolites.

Currently there are no convenient methods for quantitative measurement of all four nucleotides NAD+, NADH, NADP+ and NADPH from one biological sample. In addition, the prior art methods are considered unreliable because of, for example, non-linear response, long incubation time, requirement to do separate extractions for the different metabolites, or the fact that the results are typically given only as ratios, not absolute amounts described by concentration, hindering comparison of results between analysis sets or different research laboratories.

Furthermore, none of the prior art methods describe measurement of individual concentrations of NAD metabolites, e.g. individual concentrations of all four NAD metabolites, in whole-blood samples. Blood is particularly difficult for said analyses due to high concentration of hemoglobin.

Indeed, there remains a significant, long-felt, acute and unmet need for a simple, effective and specific method and tools for determining concentrations of all four NAD metabolites separately or NAD balance from a single sample. Development of such methods would provide a significant advance in the field of personalized medicine and for the pharmaceutical industry as it would allow targeted treatment of individuals who would benefit from treatments, such as treatment with, e.g. NAD-boosters, a field exponentially growing around the world.

SUMMARY OF THE INVENTION

The present invention has overcome the problems of the prior art methods for measuring concentrations of NAD metabolites in a biological sample, including a whole blood sample, said problems including but not limited to 1) instability of the reduced and oxidized NAD metabolites at different pH; 2) most of NAD metabolites in the cell being protein-bound and 3) stability of reduced NAD metabolites, namely, reduced NAD metabolite forms being prone to degradation at physiological pH.

One aspect of the invention is based on a method for preparing an extract comprising all four NAD metabolites from a biological sample taken from a subject. The method enables efficient extraction of the NAD metabolites from the sample and allows maintaining said metabolites in the extract without degradation.

Another aspect of the present invention enables separating all four NAD metabolites from a sample as well as measuring the amount of any one of these metabolites or the amount of any combination thereof. An easy-to-use method of the present invention can be used to measure the levels of all four NAD metabolites separately, e.g. from a blood sample. The method allows extraction and analysis from very small amounts of sample, such as from a single drop of blood. The objects of the invention, namely a method for extracting metabolites (e.g. intracellular metabolites) and a method for determining amounts of NAD+, NADP+, NADH, NADPH; NAD+/NADH ratio, NADPH/NADP+ ratio, NAD pool (NAD+ and NADH together), and/or NADP pool (NADP+ and NADPH together) from a sample obtained from a subject, and tools related thereto, are achieved by utilizing a specific combination of method steps or a specific combination of reagents.

Indeed, the superiority of the present invention, when compared to the prior art, is the ability to preserve and measure individual concentrations of all four NAD metabolites NAD+, NADH, NADP+ and NADPH to determine 1) sufficiency of vitamin B3, and/or 2) ratios of NAD+/NADH and NADPH/NADP+ as sensitive indicators of metabolic or pathological changes or need for medical intervention in the body. Furthermore, the present invention allows use of individual concentrations of any one or more of NAD metabolites or pools of any of NAD metabolites as sensitive indicators of metabolic or pathological changes. Importantly, measured individual concentrations of any of NAD metabolites can be used as independent biomarkers for normal and/or pathological metabolic changes as well as they can be integrated into a set of biomarkers for a specific condition. Metabolic changes can include e.g. those caused by normal or pathological metabolic alterations or by drugs (such as NAD-boosters).

The present invention is based on the idea of splitting an extract of a sample comprising all four NAD metabolites NAD+, NADP+, NADH and NADPH into two parts for stabilizing either reduced or oxidized forms of NAD metabolites. Furthermore, each of the two parts stabilized with either reduced or oxidized forms of NAD metabolites can be further divided into two parts for cyclic enzymatic reactions for determining the individual amounts of NAD metabolites. The present invention allows collection of data on systemic levels of NAD metabolites.

The present invention provides a quantitative method and enables assay readout to be measurable e.g. by a plate-reader spectrophotometer, easily accessible in routine diagnostic and research laboratories and suitable for analyzing large amounts of samples. Additionally, the colorimetric assay suitable for the present invention allows production of a linear response improving the accuracy of the assay.

In summary, the methods, kit and tools (including but not limited to e.g. reagents and/or wells) of the present invention are simple, reproducible and inexpensive. They do not require any special equipment or lab skills and are easy to use in almost any public laboratory. The methods, kits and tools can be applied in fundamental research on NAD metabolism as well as in clinical studies involving human subjects where there is need for NAD metabolites to be monitored in tissue samples, e.g. in the blood. Any method, kit or tools of the present invention can be used for determining or measuring the redox status of the cell or body of a subject. Compared to the prior art the present invention is not limited by a sample type and allows normalization of the results on protein amount and/or tissue mass in the tissue sample, or the volume in case of a blood sample.

The methods and tools of the present invention can be applied to both analyzing individual samples and high throughput screening, and can be applied to the diagnostics of a range of diseases. For example, the present invention can be used for assessing the need for a vitamin B3 supplement e.g. in case of suspected vitamin B3deficiency that can cause pellagra or in case of metabolic disturbance or disease, such as mitochondrial myopathy, accompanied by NAD+ drop in a tissue or several tissues. The present invention can also be used for monitoring patients taking supplements and determining the appropriate dose. The invention can also be combined with drug screening e.g. in the case of diseases where NAD metabolite concentrations and/or ratios change in response to a disease—improving NAD levels e.g. returning NAD levels to a normal range can be used as an indication of a drug's effectiveness and the patient's improving condition. Both of these are important not only for monitoring the effect of current treatments, but also for developing new treatments for disorders that are caused by imbalances in the NAD metabolites.

Indeed, the method and kit of the present invention can be used for determining and diagnosing specific disorders and monitoring the effectiveness of the current and novel treatments on the disorders.

Specifically, the present invention relates to a method for determining amounts of NAD+, NADP+, NADH, NADPH; NAD+/NADH ratio, NADPH/NADP+ ratio, NAD pool (NAD+ and NADH together), and/or NADP pool (NADP+ and NADPH together), in a sample obtained from a subject, wherein the method comprises steps A; B or C; and D (e.g. A and B and D; A and C and D):

A) obtaining an extract comprising NAD metabolites NAD+, NADP+, NADH and NADPH of a sample e.g. by contacting a sample with pre-heated non-buffered alcohol solution, and B) i) stabilizing NAD+ and NADP+ and eliminating NADH and NADPH (e.g. by acidic treatment) in a first part of the extract, and/or stabilizing NADH and NADPH and eliminating NAD+ and NADP+ (e.g. by alkali treatment with heating) in a second part of the extract for determining amounts of NAD+, NADP+, NADH, NADPH; and carrying out one or more of the following B ii)-v), ii) contacting NAD+ of the first part of the extract with a first NAD-specific enzyme in the presence of a detection system comprising an electron carrier, chromogen and non-ionic detergent to obtain an enzymatic reaction for determining amount of NAD+, iii) contacting NADH of the second part of the extract with a first NAD-specific enzyme in the presence of a detection system comprising an electron carrier, chromogen and non-ionic detergent to obtain an enzymatic reaction for determining amount of NADH, iv) contacting NADP+ of the first part of the extract with a second NADP-specific enzyme in the presence of a detection system comprising an electron carrier, chromogen and non-ionic detergent to obtain an enzymatic reaction for determining amount of NADP+, and/or v) contacting NADPH of the second part of the extract with a second NADP-specific enzyme in the presence of a detection system comprising an electron carrier, chromogen and non-ionic detergent to obtain an enzymatic reaction for determining amount of NADPH; and/or C) i) contacting NAD+ and NADH (together) of a third part of the extract with a first NAD-specific enzyme in the presence of a detection system comprising an electron carrier, chromogen and non-ionic detergent to obtain an enzymatic reaction for determining amount of NAD pool, and/or ii) contacting NADP+ and NADPH (together) of a fourth part of the extract with a second NADP-specific enzyme in the presence of a detection system comprising an electron carrier, chromogen and non-ionic detergent to obtain an enzymatic reaction for determining amount of NADP pool; and D) i) determining amounts of NAD+, NADP+, NADH, NADPH in the sample e.g. by comparing the response of a detection system to added extract with the response of standards with known concentrations to find concentration of NAD metabolite in the extract followed by normalization on protein content, tissue mass or volume of the sample and/or calculation of NAD+/NADH ratio, NADPH/NADP+ ratio and/or NAD pool (NAD+ and NADH together) and/or NADP pool (NADP+ and NADPH together), or e.g. by comparing the change in the absorbance of chromogen in the reaction with added extract with the change in the absorbance of chromogen in the reactions with added known amounts of metabolite standards to find concentration of NAD metabolite in the extract followed by normalization on protein content, tissue mass or volume of the sample and/or calculation of NAD+/NADH ratio, NADPH/NADP+ ratio, NAD pool (NAD+ and NADH together) and/or NADP pool (NADP+ and NADPH together), or ii) determining amounts of NAD pool and/or NADP pool in the sample by comparing the response of a detection system to added extract with the response of standards with known concentrations to find concentration of NAD metabolite in the extract followed by normalization on protein content, tissue mass or volume of the sample.

Also, the present invention relates to a kit comprising a detection system comprising an electron carrier, chromogen and non-ionic detergent for determining amounts of NAD+, NADP+, NADH, NADPH; NAD+/NADH ratio, NADPH/NADP+ ratio, NAD pool, and/or NADP pool from a sample of a subject; and/or comprising (e.g. optionally comprising) a chromogen for determining GSH, GSSG and/or GSH/GSSG ratio from the sample of a subject. In one aspect, the kit comprises an extraction solution, stock solutions of standards, stop solution, detection system comprising an electron carrier, chromogen, non-ionic detergent and NAD- and NADP-specific enzymes for determining NAD+, NADP+, NADH, NADPH, NAD pool, and/or NADP pool from a sample of a subject, and optionally comprising a chromogen and GSH-specific enzyme for determining GSH and GSSG from the sample of a subject.

Still, the present invention relates to use of the kit of the present invention for determining amounts of NAD+, NADP+, NADH, NADPH; NAD+/NADH ratio, NADPH/NADP+ ratio, NAD pool, NADP pool, GSH, GSSG and/or GSH/GSSG ratio or changes thereof in a sample of a subject.

Still, the present invention relates to a method for preparing an extract comprising metabolites (e.g. intracellular metabolites of a sample) such as NAD+, NADP+, NADH and NADPH from a (biological) sample, such as a solid tissue or blood, for example, whole blood sample taken from a subject, wherein the method comprises contacting the sample with pre-heated non-buffered alcohol solution (e.g. at a temperature of at least about 40° C., for example 40-80° C., 45-80° C., 50-80° C., 60-80° C., or, for example, 65-80° C.) to obtain a mixture of the sample and the alcohol solution, cooling down the obtained mixture, for example by transferring the solution on ice, and removing precipitated polypeptides from the mixture to obtain an extract comprising metabolites such as NAD+, NADP+, NADH and NADPH. Alternatively, the present invention relates to a method for preparing an extract comprising metabolites (e.g. intracellular metabolites of a sample) such as NAD+, NADP+, NADH and NADPH from a sample of a subject, wherein the method comprises allowing a sample of a subject to contact with an alcohol solution at a high temperature to obtain a mixture of the sample and the alcohol solution, cooling down the obtained mixture, and removing precipitated polypeptides from the mixture to obtain an extract comprising metabolites such as NAD+, NADP+, NADH and NADPH.

Still, the present invention relates to an extract comprising metabolites (e.g. intracellular metabolites of a sample) such as NAD+, NADP+, NADH and NADPH, wherein the extract has been prepared with the method of the present invention.

Still furthermore, the present invention relates to a method for determining the amounts of NAD+, NADP+, NADH, NADPH; NAD+/NADH ratio, NADPH/NADP+ ratio, NAD pool, and/or NADP pool from a sample of a subject, wherein the method comprises preparing an extract comprising NAD+, NADP+, NADH and NADPH metabolites from a sample of a subject according to a method of the present invention and determining or measuring amounts or concentrations of NAD+, NADP+, NADH, NADPH; NAD+/NADH ratio, NADPH/NADP+ ratio, NAD pool, and/or NADP pool e.g. according to a method of the present invention.

Still furthermore, the present invention relates to a method for determining abnormal NAD amounts or ratios in a disorder, or a method for determining manifestation, status, progression or follow-up of a disorder related to altered amount or balance of NAD metabolites, wherein the method comprises determining and/or measuring (e.g. amounts or concentrations of) NAD+, NADP+, NADH, NADPH, NAD+/NADH ratio, NADPH/NADP+ ratio, NAD pool, and/or NADP pool from a sample of a subject (e.g. a whole blood sample). Evidence that blood concentrations of NAD metabolites reflect disturbances in NAD-dependent metabolism in human body comes from mitochondrial myopathy, a disease caused by mutations of mitochondrial DNA, such as single large deletions or point mutations of mitochondrial DNA, or nuclear genome-encoded mitochondrial DNA maintenance proteins, such as mitochondrial helicase TWINKLE or DNA polymerase gamma or functionally linked proteins. These diseases are characterized by drop of NAD+ concentration in the muscle and blood. Observed correlation between concentration of NAD+ in diseased muscle and blood in these patients suggests that blood concentrations of NAD metabolites can reflect disturbances of NAD metabolism caused by a disease in a solid tissue. Evidence that NAD metabolism is affected in different other pathologies comes from studies on animal models and on cell cultures. Data on humans are scarce due to absence of convenient detection method to analyze changes in concentrations of NAD metabolites in blood in response to disease. The disorder with suspected disturbance of NAD metabolism or with abnormal NAD amounts or ratios can be selected e.g. from the group comprising or consisting of diseases with previously reported contribution of mitochondrial dysfunction, i.e. diabetes type I or II, muscle disease, fatty liver disease (non-alcoholic and acquired alcoholic), obesity, Parkinson's disease, Alzheimer's disease, other neurodegenerative diseases such as multiple sclerosis; lung disease, kidney disease, liver disease, thyroid disease, cardiac or cerebral stroke, chronic fatigue syndrome, ataxia disease, ocular disease, mitochondrial disorder, metabolic disorder including inherited and non-inherited, anorexia, cachexia, viral or bacterial infection or related secondary disease such as immune reaction, endocrine disorders, nutrient deficiency, and cancer (such as a breast, colon, stomach, brain, pancreas, prostate, ovary, liver, lung or skin cancer, or leukemia), of children, teenagers or adults.

Still furthermore, the present invention relates to a kit for determining abnormal NAD-amounts or ratios in a disorder, for determining a disorder, and/or for determining manifestation, status, progression, treatment response or follow-up of a disorder related to altered amount or balance of NAD metabolites, wherein the kit comprises a detection system comprising an electron carrier, chromogen and non-ionic detergent for determining NAD+, NADP+, NADH, NADPH, NAD+/NADH ratio, NADPH/NADP+ ratio, NAD pool, and/or NADP pool from a sample of a subject (e.g. according to the kit of the present invention). In one aspect, the present invention relates to a kit for determining abnormal NAD amounts or ratios in a disorder, for determining a disorder, and/or for determining manifestation, status, progression, treatment response or follow-up of a disorder related to altered amount or balance of NAD metabolites, wherein the kit comprises an extraction solution, stock solutions of standards, stop solution, detection system comprising an electron carrier, chromogen, non-ionic detergent and NAD- and NADP-specific enzymes for determining NAD+, NADP+, NADH, NADPH, NAD+/NADH ratio, NADPH/NADP+ ratio, NAD pool, and/or NADP pool from a sample of a subject. The disorder can be selected e.g. from the group comprising or consisting of diseases with previously reported contribution of mitochondrial dysfunction, i.e. diabetes type I or II, muscle disease, fatty liver disease (non-alcoholic and acquired alcoholic), obesity, Parkinson's disease, Alzheimer's disease, other neurodegenerative diseases such as multiple sclerosis; lung disease, kidney disease, liver disease, thyroid disease, cardiac or cerebral stroke, chronic fatigue syndrome, ataxia disease, ocular disease, mitochondrial disorder, metabolic disorder including inherited and non-inherited, anorexia, cachexia, viral or bacterial infection or related secondary disease such as immune reaction, endocrine disorders, nutrient deficiency, and cancer (such as a breast, colon, stomach, brain, pancreas, prostate, ovary, liver, lung or skin cancer, or leukemia), of children, teenagers or adults.

Still furthermore, the present invention relates to use of the kit of the present invention for determining NAD metabolite amounts or ratios to determine manifestation, status, progression, treatment response, or follow-up of a disorder selected from the group comprising or consisting of diabetes type I or II, muscle disease, fatty liver disease (non-alcoholic and acquired alcoholic), obesity, Parkinson's disease, Alzheimer's disease, other neurodegenerative diseases such as multiple sclerosis; lung disease, kidney disease, liver disease, thyroid disease, cardiac or cerebral stroke, chronic fatigue syndrome, ataxia disease, ocular disease, mitochondrial disorder, metabolic disorder including inherited and non-inherited, anorexia, cachexia, viral or bacterial infection or related secondary disease such as immune reaction, endocrine disorders, nutrient deficiency, and cancer (such as a breast, colon, stomach, brain, pancreas, prostate, ovary, liver, lung or skin cancer, or leukemia), of children, teenagers or adults.

Still furthermore, the present invention relates to use of concentrations of NAD+, NADP+, NADH, NADPH, NAD+/NADH ratio, NADPH/NADP+ ratio, NAD pool, and/or NADP pool for determining manifestation, status, progression or treatment response of a disorder or for diagnosing a disorder e.g. selected from the group consisting of diseases with previously reported contribution of mitochondrial dysfunction, i.e diabetes type I or II, muscle disease, fatty liver disease (non-alcoholic and acquired alcoholic), obesity, Parkinson's disease, Alzheimer's disease, other neurodegenerative diseases such as multiple sclerosis; lung disease, kidney disease, liver disease, thyroid disease, cardiac or cerebral stroke, chronic fatigue syndrome, ataxia disease, ocular disease, mitochondrial disorder, metabolic disorder including inherited and non-inherited, anorexia, cachexia, viral or bacterial infection or related secondary disease such as immune reaction, endocrine disorders, nutrient deficiency, and cancer (such as a breast, colon, stomach, brain, pancreas, prostate, ovary, liver, lung or skin cancer, or leukemia), of children, teenagers or adults, or determining the effectiveness of treatment for a disease or disorder related to altered amount or balance of NAD metabolites.

Still furthermore, the present invention relates to use of concentrations of NAD+, NADP+, NADH, NADPH, NAD+/NADH ratio, NADPH/NADP+ ratio, NAD pool, and/or NADP pool for determining manifestation, status, progression or treatment response of a disorder or for diagnosing a disorder e.g. selected from the group consisting of diseases with previously reported contribution of mitochondrial dysfunction, i.e diabetes type I or II, muscle disease, fatty liver disease (non-alcoholic and acquired alcoholic), obesity, Parkinson's disease, Alzheimer's disease, other neurodegenerative diseases such as multiple sclerosis; lung disease, kidney disease, liver disease, thyroid disease, cardiac or cerebral stroke, chronic fatigue syndrome, ataxia disease, ocular disease, mitochondrial disorder, metabolic disorder including inherited and non-inherited, anorexia, cachexia, viral or bacterial infection or related secondary disease such as immune reaction, endocrine disorders, nutrient deficiency, and cancer (such as a breast, colon, stomach, brain, pancreas, prostate, ovary, liver, lung or skin cancer, or leukemia), of children, teenagers or adults, or determining the effectiveness of treatment for a disease or disorder related to altered amount or balance of NAD metabolites.

Other objects, details and advantages of the present invention will become apparent from the following drawings, detailed description and examples.

BRIEF DESCRIPTION OF THE DRAWINGS

FIG. 7A shows healthy controls (age 18-30 years, n=86), healthy controls (age 31-40 years, n=63), healthy controls (age 41-50 years, n=64), and healthy controls (age 51-60 years, n=61). FIG. 7B shows healthy controls (age 61-70 years, n=25), breast cancer (n=22), brain cancer (n=3), and colon cancer (n=15). Sources for the samples are the same as described in FIGS. 4A-4C.

FIG. 8A shows stomach cancer (n=9), pancreatic cancer (n=15), prostate cancer (n=16), and ovarian cancer (n=12). FIG. 8B shows lung cancer (n=15), liver cancer (n=3), acute leukemia (n=12) and chronic leukemia (n=4). Sources for the samples are the same as described in FIGS. 4A-4C.

FIG. 9A shows Parkinson's disease (n=15), Alzheimer's disease (n=15), melanoma (n=16), and Diabetes type I (n=7). FIG. 9B shows Diabetes type II (n=15), chronic fatigue syndrome (n=3), progressive external ophthalmoplegia (PEO) (n=5) and mitochondrial recessive ataxia syndrome (MIRAS) (n=8). Sources for the samples are the same as described in FIGS. 4A-4C, except that PEO and MIRAS patients are from sample collection of Prof. Anu Wartiovaara laboratory.

DETAILED DESCRIPTION OF THE INVENTION

Figure 1:
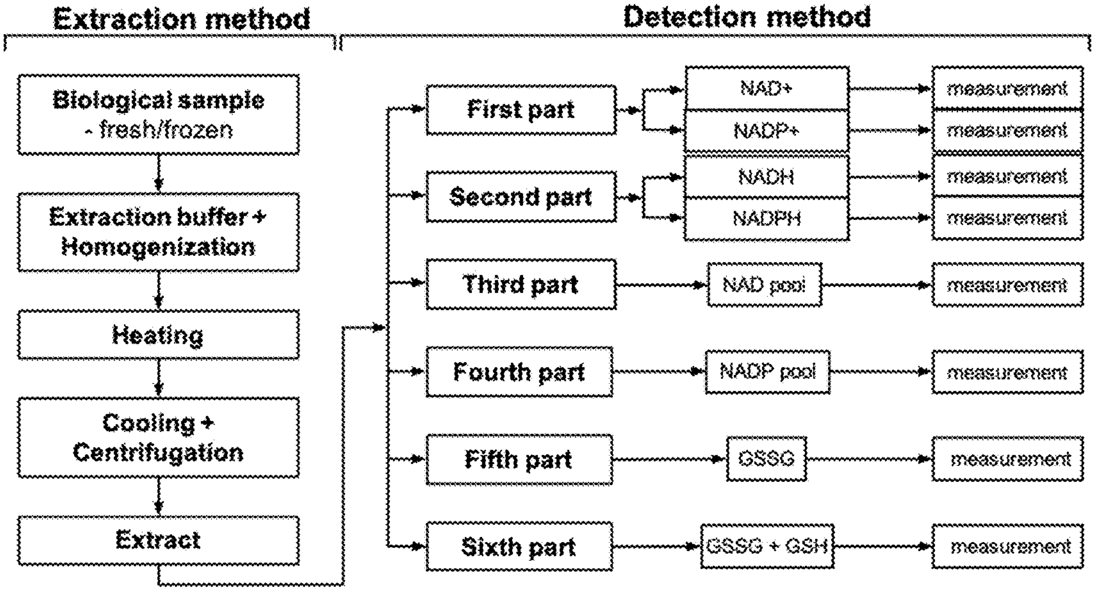
FIG. 1 shows schematically an example of an extraction method and/or detection method of the present invention for determining amounts of NAD+, NADP+, NADH, NADPH, NAD+/NADH ratio, NADPH/NADP+ ratio, NAD pool, and/or NADP pool, and optionally GSH, GSSG and/or GSH/GSSG ratio, from a sample of a subject. The extraction method is based on release of NAD metabolites from protein-bound state into solution upon protein unfolding caused by sample contact with pre-heated non-buffered alcohol solution. Unfolded proteins are removed from the extract by precipitation on ice followed by centrifugation. The method or kit can utilize at least "the first part" (NAD+ and/or NADP+) or at least "the second part" (NADH and/or NADPH), or at least "the first part" and "the second part". In one embodiment the method or kit comprises any combination of "the first part", "the second part", "the third part", "the fourth part", and optionally "the fifth part", and "the sixth part". In one example NAD+ concentration of "the first part" can be measured in a separate plate (e.g. plate no 1), NADP+ concentration of "the first part" can be measured in a separate plate (e.g. plate no 2), NADH concentration of "the second part" can be measured in a separate plate (e.g. plate no 3), NADPH concentration of "the second part" can be measured in a separate plate (e.g. plate no 4), a pool of NAD+ and NADH of "the third part" can be measured in a separate plate (e.g. plate no 5), and/or a pool of NADP+ and NADPH of "the fourth part" can be measured in a separate plate (e.g. plate no 6), GSSG concentration of "the fifth part" can be measured in a separate plate (e.g. plate no 7); and/or GSSG and/or GSH concentrations of "the sixth part" can be measured in a separate plate (e.g. plate no 8).

Prior art does not present an universal method for measuring individual concentrations of pyridine nucleotides NAD+, NADH, NADP+, and NADPH in any type of biological sample, e.g. for example cells, tissues and blood. For example, U.S. Pat. No. 6,287,796 B1 describes method for extraction and measurement of NAD metabolites from blood and nonhematologic tissues, but it can measure only NAD pool (NAD+ and NADH together) and NADP pool (NADP+ and NADPH together) without separation on individual metabolites. One of the reasons for this is that this prior art uses strong acid in extraction process to remove proteins which results in very rapid protein precipitation preventing efficient release of the metabolites into a solution. In addition, usage of strong acid results in degradation of reduced forms of NAD metabolites. Additionally, this prior art also uses strong alkali for acid neutralization and alkali conditions destabilize oxidized forms of metabolites. Other two examples of prior art, e.g. Gonzalez B., Francois J. and Renaud M (1997) Yeast, Vol. 13, pp 1347-1356 and Sellick C. A. et al (2010) Metabolomics, Vol. 6, pp. 427-438 describe methods for measurement of concentrations of NAD metabolites in cells using ethanol for extraction. Gonzalez et al (1997) uses absolute boiling ethanol at 90° C. for extraction of NAD metabolites among other cellular metabolites from Chinese hamster ovary cell culture. The boiling ethanol results in very low yield of NAD and NADH. This is not surprising because in this condition proteins precipitate very efficiently and all NAD metabolites bound to proteins end up in the precipitate. Sellick et al present a method for NAD metabolites measurement in yeast culture. This prior art uses boiling 75% ethanol buffered with 70 mM Hepes pH 7.5 followed by cooling and evaporation of liquid from the extract. The residue is resuspended in water and insoluble material is removed by centrifugation. These prior art extraction conditions are not tested by authors for any other sample type. Due to the fact that boiling ethanol is causing immediate protein precipitation the method by Sellick et al is unsuitable for samples with high protein content like blood. In commercial kits, e.g. for example BioVision NAD+/NADH quantification colorimetric kit Cat #K337-100 extraction of NAD metabolites is developed for cells and tissues, not for blood. Extraction conditions do not involve denaturation of proteins and therefore there is high risk of interconversion of NAD metabolites (NAD+ to NADH and back; and same for NADP+ and NADPH pair) catalyzed by NAD-dependent enzymes present in the extract. This results in errors of quantification of NAD metabolites.

The inventors here have solved the problems of insufficient metabolite release from the proteins in a tissue sample as well as the issues relating to the stability of the metabolites during the extraction protocol and have developed 1) a method for preparing an extract comprising NAD+, NADP+, NADH, NADPH and 2) a method and kit for determining amounts of NAD+, NADP+, NADH, NADPH, NAD+/NADH ratio, NADPH/NADP+ ratio, NAD pool, and/or NADP pool by one sample analysis which suits requirements of a clinical laboratory, and 3) a platform for high-throughput analysis of NAD+, NADP+, NADH, NADPH concentrations in a large amount of samples. Indeed, the present invention enables measuring NAD+: NADH and NADP+:NADPH balances in animal tissues, cells and blood, including whole blood. Accurate estimation of oxidative damage in the body (e.g. on the systemic level) can be carried out by the methods, kit and tools of the present invention. Because the method can provide a quantitative output, it also allows comparison of the results between runs and laboratories.

The method of the present invention for determining amounts of NAD metabolites in a sample obtained from a subject comprises steps A; B or C; and D (e.g. A and B and D; A and C and D):

A) obtaining an extract comprising NAD metabolites NAD+, NADP+, NADH and NADPH of a sample by contacting a sample with pre-heated to at least 40° C. non-buffered alcohol solution, and B) i) stabilizing NAD+ and NADP+ and eliminating NADH and NADPH by acidic treatment in a first part of the extract, and/or stabilizing NADH and NADPH and eliminating NAD+ and NADP+ by alkali treatment with heating in a second part of the extract for determining amounts of NAD+, NADP+, NADH, NADPH; and carrying out one or more of the following B ii)-v), ii) contacting NAD+ of the first part of the extract with a first NAD-specific enzyme in the presence of a detection system comprising an electron carrier, chromogen and non-ionic detergent to obtain an enzymatic reaction for determining amount of NAD+, iii) contacting NADH of the second part of the extract with a first NAD-specific enzyme in the presence of a detection system comprising an electron carrier, chromogen and non-ionic detergent to obtain an enzymatic reaction for determining amount of NADH, iv) contacting NADP+ of the first part of the extract with a second NADP-specific enzyme in the presence of a detection system comprising an electron carrier, chromogen and non-ionic detergent to obtain an enzymatic reaction for determining amount of NADP+, and/or v) contacting NADPH of the second part of the extract with a second NADP-specific enzyme in the presence of a detection system comprising an electron carrier, chromogen and non-ionic detergent to obtain an enzymatic reaction for determining amount of NADPH; and/or C) i) contacting NAD+ and NADH together of a third part of the extract with a first NAD-specific enzyme in the presence of a detection system comprising an electron carrier, chromogen and non-ionic detergent to obtain an enzymatic reaction for determining amount of NAD+ pool, and/or ii) contacting NADP+ and NADPH together of a fourth part of the extract with a second NADP-specific enzyme in the presence of a detection system comprising an electron carrier, chromogen and non-ionic detergent to obtain an enzymatic reaction for determining amount of NADP pool; and D) i) determining amounts of NAD+, NADP+, NADH and/or NADPH in the sample e.g. by comparing the change in the absorbance of chromogen in the reaction with added extract with the change in the absorbance of chromogen in the reactions with added known amounts of metabolite standards to find concentration of NAD metabolite in the extract followed by normalization on protein content, tissue mass or volume of the sample and/or calculation of NAD+/NADH ratio, NADPH/NADP+ ratio and/or NAD pool (NAD+ and NADH together) and/or NADP pool (NADP+ and NADPH together) or ii) determining amounts of NAD pool and/or NADP pool in the sample by comparing the response of a detection system to added extract with the response of standards with known concentrations to find concentration of NAD metabolite in the extract followed by normalization on protein content, tissue mass or volume of the sample.

As used herein the term "determining/determination" refers to measuring/measurement and/or calculating/calculation. A person skilled in the art is able to recognise when the term determining/determination refers only to measuring/measurement or calculating/calculation or when it covers both measuring/measurement and calculating/calculation.

Extraction of NAD metabolites from the whole blood is a challenging task, because whole blood has a very high protein content (approx. 100 mg/mL in human blood) with hemoglobin as the main fraction. During denaturation process unfolded proteins have to be maintained for some time in a soluble state to release NAD metabolites into solution. During denaturation in alkaline conditions hemoglobin forms transient intermediate which is thought to chemically destroy reduced pyridine nucleotides. Therefore, extraction of NADPH and NADH cannot be done in alkali conditions.

A single extract comprising NAD+, NADP+, NADH and NADPH for the method or kit of the present invention for determining amounts of each of the four NAD metabolites can be obtained only by extraction method described in the present invention. In one aspect, the extraction method of the present invention comprises contacting the sample with non-buffered alcohol solution, such as ethanol-water solution, pre-heated to a high temperature. For obtaining an extract of a blood, tissue or cells sample e.g. for the present invention EtOH is one of the suitable reagents (optionally with a non-ionic surfactant, such as Triton™ (polyethylene glycol tert-octylphenyl ether)). In one embodiment, the extraction conditions do not include any acidic protein precipitants like trichloroacetic acid or perchloric acid which are known to be inhibitors of enzymatic activities in assays based on enzymatic reactions. The extract obtained using the extraction method of the present invention can also be called as a "primary extract" as it comprises all four NAD metabolites and also contains approximately 1500 other cellular metabolites which include reduced and oxidized forms of glutathione GSH and GSSG. The extract obtained using the extraction method of the present invention is compatible with mass spectrometry analysis. Cellular metabolites are stable in the primary extract and represent a snap-shot of cellular metabolism.

In one aspect the method for determining amounts of NAD metabolites, and optionally reduced and oxidized forms of glutathione GSH and GSSG from a biological sample, such as cells or tissue, such as blood, for example whole blood, comprises preparing the extract comprising NAD+, NADP+, NADH and NADPH from the sample, wherein the method comprises contacting the biological sample with pre-heated non-buffered alcohol solution at a high temperature (e.g. at a temperature of 40-80° C., 45-80° C., 50-80° C., 60-80° C., or, for example, 65-80° C.) to obtain a mixture of the sample and the alcohol solution, cooling down the obtained mixture, and removing precipitated polypeptides from the mixture to obtain an extract comprising NAD+, NADP+, NADH and NADPH.

The present invention also relates to a method for preparing an extract comprising NAD+, NADP+, NADH and NADPH from a sample of a subject, wherein the method comprises contacting a biological sample taken from a subject with pre-heated non-buffered alcohol solution, such as ethanol solution, at a high temperature (e.g. at a temperature of 40-80° C., 45-80° C., 50-80° C., 60-80° C., or, for example, 65-80° C.) to obtain a mixture of the sample and the alcohol solution, cooling down the obtained mixture, for example placing it on ice, and removing precipitated polypeptides, for example by centrifugation, from the mixture to obtain an extract comprising NAD+, NADP+, NADH and NADPH.

In one aspect of the method for determining NAD metabolites or preparing an extract, the non-buffered alcohol solution can comprise ethanol, methanol and/or isopropanol; or the alcohol solution can be an ethanol, methanol or isopropanol solution in water. In one embodiment the alcohol concentration of the alcohol solution is about 30-80%, 40-70%, 40-60%, 40-50%, 50-70%, 50-60%, 50% or 60%.

In the methods of the present invention, the alcohol solution is pre-heated to a temperature of at least about 40° C., for example 40-80° C., 40-60° C., 45-80° C., 50-80° C., 60-80° C., 70-80° C., 60° C. or 75° C. In one aspect the contacting time at a high temperature is, for example about 10 seconds-10 minutes, about 30 seconds-5 minutes, or about 1 minute.

Cooling down the obtained mixture of the sample and the alcohol solution can be carried out e.g. by placing the mixture on ice. A period for cooling down can be e.g. about 30 seconds-30 minutes, 1-10 minutes, 5-10 minutes or 3-7 minutes.

In one embodiment, after cooling down the mixture the precipitated polypeptides are removed by centrifugation, optionally at about +4° C., e.g. for at least 5 to at about 20 minutes, for example about 10 minutes (e.g. 20000×g for 5-15 min, such as 10 min).

In one embodiment the method for preparing an extract further comprises selective stabilization of either reduced or oxidized forms of NAD metabolites in the parts of an extract followed by separate determining of amounts of any metabolite (e.g. intracellular metabolites of a sample); or amounts of NAD+, NADP+, NADH, NADPH or NAD pool, and/or NADP pool from the extract (e.g. according to any method of the present invention) and optionally GSH and GSSG; or the method further comprises simultaneous determination of NAD+/NADH, NADPH/NADP+ and/or GSH/GSSG ratios or of NADPH/NADP+ and GSH/GSSG ratios from the same sample for determining or measuring the redox status of the cell or body.

In one aspect, the mixture of the sample and the alcohol solution is a homogenate. As used herein "a homogenate" refers to the mixture of tissues and/or cells and the alcohol solution, wherein one or more cell structures have been disrupted e.g. mechanically allowing the organelles of the disrupted cells to be released to the solution. For example, filtering can be used for separating a solution from the cells, tissues and/or parts thereof.

In one aspect of the invention, all NAD metabolites are stable in the non-buffered alcohol solution such as EtOH, thus allowing them to be extracted all at once and to be comprised in a single extract; and/or all NAD metabolites are stable in the non-buffered alcohol solution (such as EtOH) at high temperatures.

The extract obtained with the extraction method, i.e., the primary extract, of the present invention comprises all four forms of the NAD metabolites, which were found to be stable in non-buffered alcohol solution. The primary extract also comprises GSH and GSSG.

The obtained extract can be divided into multiple parts, such as two, three, four, five, six, seven, eight, nine or ten parts, depending on which or how many of the NAD metabolites NAD+, NADP+, NADH or NADPH, their pools and reduced or oxidized forms of glutathione (GSH or GSSG) are to be detected, measured or analyzed in the detection methods of the invention.

In one aspect, stabilizing NAD+ and NADP+ and eliminating NADH and NADPH in a first part of the extract is performed by contacting the extract with HCl e.g. at temperatures in the range of 20-25° C., and/or stabilizing NADH and NADPH and eliminating NAD+ and NADP+ in a second part of the extract can be carried out e.g. by contacting the extract with NaOH e.g. with a short exposure to high temperature. For example, the final concentration of NaOH or HCl in the sample according to the present invention can be e.g. 0.01-0.1M such as 0.04M. The short exposure to high temperature can be performed at e.g. 60-90° C. such as 80° C. for e.g. 1-5 min such as 1 min.

In one aspect of the method, measurement of stabilized NAD metabolites is performed within one hour after stabilization.

Figure 2:
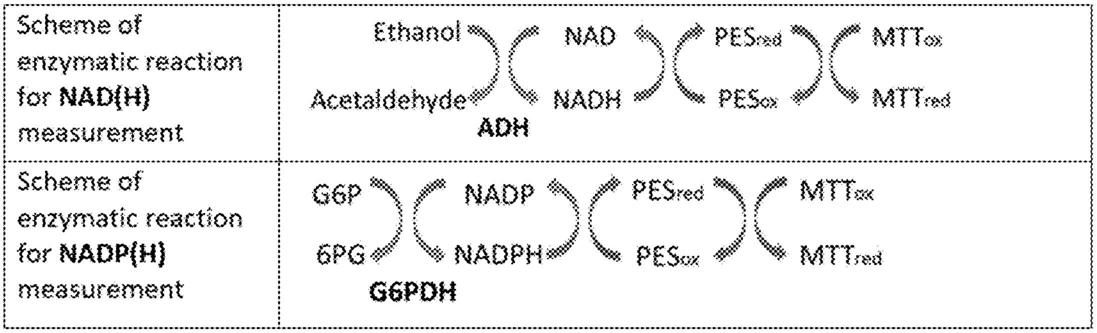
FIG. 2 shows a schematic representation of enzymatic assays suitable for use in the detection method or kit or with the tools of the present invention.

The principle of the method for determining amounts of NAD metabolites and kit of the present invention is a cyclic enzymatic reaction (see e.g. FIG. 2). In the assay, an enzyme, which specifically recognizes and uses NAD+ or NADP+ as substrate is used for the reaction producing NADH or NADPH. Each enzyme reduces an oxidized NAD metabolite and the reduced form then donates electron to an electron carrier (e.g. Phenazine ethosulfate (PES)), which then passes the electron to the final electron acceptor (e.g. tetrazolium bromide (MTT)). As a result, NAD(P)H is converted back to the oxidized form and it enters the next catalytic cycle of the enzymatic reaction while the final electron acceptor (e.g. MTT) is converted into its reduced form (if MTT is used, its reduced form is formazan). The detection comprises measuring absorption change of MTT upon its reduction in the assay reaction (e.g., formazan can be detected at a wavelength 573 nm). Measured change in absorption of chromogen is also called assay response.

In one aspect, the kit of the present invention comprises at least reagents for extracting NAD metabolites from a biological sample. In another aspect, the kit comprises reagents for extracting NAD metabolites from the biological sample and for determining the amounts or ratios of NAD metabolites, and optionally also glutathione. Examples of reagents include, but are not limited to one or more suitable extraction liquid(s), reaction solutions, washing solutions, buffers, enzymes, electron carriers, chromogens, non-ionic detergent(s). The kit may further comprise reagents for performing a method for determining at least NAD metabolites. In one aspect, the kit comprises reagents for obtaining the extract from a sample. In one aspect, the kit comprises reagents for performing a cyclic enzymatic reaction. In one aspect, the kit comprises reagents for extracting GSH and GSSG and reagents for detecting or measuring the amount and/or ratio of GSH or GSSG in a biological sample.

In one aspect of any method of the invention, any enzyme suitable for the cyclic enzymatic reaction of the present invention can be used. In one aspect, the first NAD-specific enzyme utilized in the method or kit of the present invention is selected from the group consisting of an alcohol dehydrogenase, malate dehydrogenase, lactate dehydrogenase, NAD specific isocitrate dehydrogenase, glyceraldehyde-3-phosphate dehydrogenase, and any combination thereof; and/or the second NADP-specific enzyme is selected from the group consisting of a glucose-6-phosphate dehydrogenase, 6-phosphogluconate dehydrogenase, malic enzyme, NADP specific isocitrate dehydrogenase, and any combination thereof. In a very specific embodiment, the first NAD-specific enzyme is an alcohol dehydrogenase (ADH) (e.g. yeast ADH) and the second NADP-specific enzyme is a glucose-6-phosphate dehydrogenase (G6PDH) (e.g. yeast G6PDH).

In one embodiment, the detection system used in the method for determining amounts of NAD metabolites, kit or tools of present invention comprises an electron carrier, chromogen and non-ionic detergent to obtain an enzymatic reaction. In one embodiment, the electron carrier is phenazine ethosulfate (PES) and/or the chromogen is 3-(4, 5-dimethylthiazol-2-yl)-2,5-diphenyl tetrazolium bromide (MTT) for determining amounts of NAD+, NADP+, NADH, NADPH. In one embodiment, the non-ionic detergent comprises a polyethylene oxide unit or tail and is optionally selected from the group comprising but not limited to Tween® 20 (polysorbate 20), Triton™ X-100, and nonyl phenoxypolyethoxylethanol (NP-40). For example, Formula I describes an example of Triton™M X-100. The moiety in brackets in Formula I is an ethylene oxide unit. The non-ionic detergent comprising a polyethylene oxide unit can be utilized for preventing MTT aggregation upon reduction in the course of enzymatic reaction(s).

Formula I

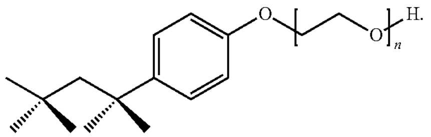

The non-ionic detergent comprising a polyethylene oxide unit can be added to any cyclic enzymatic reaction of the present invention. Presence of the non-ionic detergent comprising a polyethylene oxide unit prevents or slows down aggregation of any kind and assures low variation between replicates and high rate of enzymatic reaction in one embodiment of the method or kit of the present invention. The non-ionic detergent enables short enzymatic reaction times as well as fast assays. Addition of the non-ionic detergent to the assay can reduce the enzymatic reaction time e.g. from about 30 min-1 hr to e.g. about 5 min-25 min (such as to about 10 min). For example, the actual time for determining amounts of NAD+ and NADH according to the present invention can be e.g. 5-16 min such as 8 min or 10 min, and/or the actual time for determining NADP+ and NADPH can be e.g. 5-15 min such as 10 min.

In the methods of the prior art, MTT precipitates during the enzymatic reaction and thus reduces the reliability of the absorption measurements. Precipitation of MTT also slows down the rate of the enzymatic reaction. These two factors result in significant variation and thus make the prior art methods unpredictable and unreliable. Furthermore, precipitation of MTT result in non-linear enzymatic reaction at high concentration of metabolites, which further reduces the reliability of these methods. Addition of non-ionic detergent comprising a polyethylene oxide unit described in this invention solved all said limitations of enzymatic reactions including those with MTT.

The methods of the prior art either do not stop cyclic enzymatic reactions or stop by adding a specific inhibitor of the enzyme used in an assay (for example in BioVision NAD+/NADH quantification colorimetric kit Cat #K337-100). Advantage of the stopping step is that it allows synchronization in time of all enzymatic reactions in an assay which makes comparison of the assay responses of the extract(s) with those of standards reliable leading to accurate estimation of concentrations of NAD metabolites in the sample. However, in the prior art there is no universal stopping agent which could be used in any enzyme based assay including those for measuring concentrations of NAD metabolites. The inventors have discovered that the problem of time synchronization for all reactions in any enzyme based assay, including assays of the present invention, e.g. assay reactions of standards and assay reactions of obtained extract(s), can be solved by adding of a denaturing ionic detergent into reaction mixtures. Added denaturing ionic detergent stops the reaction by denaturation of the enzyme which catalyzes the cyclic enzymatic reaction. In one aspect, the advantage of using denaturing ionic detergent to stop the reaction is that it can be used in any assay based on enzymatic activity. Accordingly, in one aspect of the methods and kits of the invention, the enzymatic reactions of the method or kit are stopped after a suitable reaction time by contacting the enzymatic reaction mixture with an ionic detergent, for example, optionally selected from sodium dodecyl sulfate (SDS), cetyltrimethylammonium bromide (CTAB) and/or a combination thereof. For example, SDS/CTAB can be added to any cyclic enzymatic reaction of the present invention. One of the additional advantages of the stopping step is that it allows synchronizing all the enzymatic reactions, for example when multiplexed on a multi-well plate (e.g. on the plate) in time. The detergent used for stopping the reaction can be added to the enzymatic reactions at a suitable time when the enzymatic reactions need to be stopped. In one aspect, the suitable time an actual assay time is after about 5-30 min, e.g. 10-20 min (such as 10-11 min). In one aspect of the invention, the kit comprises an ionic detergent, optionally selected from sodium dodecyl sulfate (SDS), cetyltrimethylammonium bromide (CTAB) and a combination thereof, for stopping an enzymatic reaction(s).

The method and kit of the present invention enable a significantly more sensitive and consistently linear method or kit for performing such method compared to the methods described in prior art, providing a valuable tool to analyze the redox status (e.g. the systemic redox status) of the human body.

In one embodiment, in addition to determining amounts of NAD+, NADP+, NADH, NADPH, NAD+/NADH ratio, and/or NADPH/NADP+ ratio, the present extraction and detection methods or kits enable isolation and/or measurements of total pools of NAD and NADP without separation on NAD+, NADP+ and NADPH and NADPH, i.e. analyzing the primary extract without splitting it into parts for reduced and oxidized forms (see e.g. FIG. 1, "the third and fourth parts").

In addition to NAD metabolites, the extraction or determining method or kit of the present invention further allows isolation and/or measurements of concentrations of reduced and/or oxidized glutathione (GSH, GSSG), which ratio GSH/GSSG is directly dependent of NADPH/NADP+ balance. Glutathione is the major antioxidant in our cells and capable of preventing damages of cellular components caused by reactive oxygen species. The ratio of reduced glutathione to oxidized glutathione within cells is a measure of cellular oxidative stress and decreased GSH-to-GSSG ratio is indicative of cellular oxidative stress. For example, simultaneous measurement of NAD+/NADH, NADPH/NADP+ and GSH/GSSG ratios or NADPH/NADP+ and GSH/GSSG ratios from the same sample allows accurate estimation of the oxidative damage or stress in the body. As glutathione is dependent on NADPH levels, GSH and/or GSSG can be measured from the same biological samples to complement NADPH/NADP+ measurements. Concentrations and ratios of NAD+ and NADH; NADP+ and NADPH; and GSH and GSSG together can be considered as a measure of redox status of a sample. In one embodiment, the method of the present invention comprises extracting NAD metabolites together with reduced and/or oxidized forms of glutathione from a sample, to obtain an extract comprising NAD+, NADP+, NADH, NADPH, GSH and GSSG. Furthermore, the method of the present invention enables measurement of concentrations of GSH and/or GSSG using a separate enzymatic (and optionally colorimetric) assay compared to one or more enzymatic NAD metabolites assays. In one embodiment, the method of the present invention comprises determining (amount of) GSH, GSSG, and/or GSH/GSSG ratio; or the method comprises simultaneous determining of NAD+/NADH, NADPH/NADP+ and GSH/GSSG ratios or NADPH/NADP+ and GSH/GSSG ratios from the same sample for determining or measuring the redox status of the cell or body.

In one embodiment, the method of the present invention comprises i) removing GSH from a fifth part of the extract of A) by a chemical modification and contacting GSSG of the fifth part of the extract with a GSH-specific enzyme, such as glutathione reductase in the presence of added NADPH and a chromogen for determining amount of GSSG; and/or ii) contacting GSH and GSSG of a sixth part of the extract of A) with a GSH-specific enzyme, such as glutathione reductase in the presence of added NADPH and a chromogen for determining concentration of GSH pool (GSH and GSSG together).

Removal of GSH can be carried out by any suitable chemical agent, e.g. by addition of masking reagent 1-methyl-4-vinyl-pyridinium trifluoromethane sulfonate (M4VP) and/or 1-methyl-2-vinyl-pyridinium trifluoromethane sulfonate (M2VP).

In one embodiment, the reporter for determining GSH and/or GSSG is 5,5'-dithiobis(2-nitrobenzoic acid) (DTNB) also called as Ellman's reagent.

Ready reagent mixes can be used in the detection method or kit of the present invention. The reagent mix typically comprises all other reagents necessary for the reaction except the enzyme. Accordingly, the methods and kits may comprise use of containers for a reaction mix to which the suitable enzyme responsible for carrying out the reaction is added. In one aspect of the method of the invention, the first reagent combination comprising a first and/or second part of the extract, an electron carrier, chromogen and non-ionic detergent combination and the first NAD-specific enzyme are used for enzymatic reactions for determining amounts of NAD+ and/or NADH; the second reagent combination containing first and/or second part of the extract, an electron carrier, chromogen and non-ionic detergent combination and the second NADP-specific enzyme are used for enzymatic reactions for determining amounts of NADP+ and/or NADPH; and/or the third reagent combination comprising a fifth and/or sixth part of the extract, added NADPH and a repoter, and a GSH-specific enzyme, such as glutathione reductase are used for enzymatic reactions for determining amounts of GSH and/or GSSG. In one embodiment, the kit comprises the first reagent combination to be used with the first NAD-specific enzyme for determining amounts of NAD+ and/or NADH; the second reagent combination to be used with the second NADP-specific enzyme for determining amounts of NADP+ and/or NADPH; and/or the third reagent combination to be used with a GSH-specific enzyme, such as glutathione reductase for determining amounts of GSH and/or GSSG. In one embodiment, the method or kit comprises the first and second and optionally the third reagent combinations.

In one aspect, the first reagent combination comprises a buffer (such as Bicine-NaOH, e.g. pH 8.0) and a first master mix comprising e.g. EDTA, MTT, PES, a non-ionic detergent, $H_2O$ and a substrate (such as alcohol, e.g. EtOH) for the first NAD-specific enzyme (such as ADH). Substrates for the first NAD-specific enzyme include but are not limited to alcohol (e.g. EtOH) for ADH, malate for malate dehydrogenase, lactate for lactate dehydrogenase, isocitrate for NAD specific isocitrate dehydrogenase, and/or glyceraldehyde-3-phosphate for glyceraldehyde-3-phosphate dehydrogenase.

In one aspect, the second reagent combination comprises a buffer (such as Bicine-NaOH, e.g. pH 8.0) and a second master mix comprising e.g. EDTA, MTT, PES, a non-ionic detergent, $H_2O$ and a substrate (such as glucose-6-phosphate (G6P)) for the second NADP-specific enzyme (such as G6PDH). Substrates for the second NADP-specific enzyme include but are not limited to G6P for G6PDH, 6-phosphogluconate for 6-phosphogluconate dehydrogenase, malate for malic enzyme, isocitrate for NADP specific isocitrate dehydrogenase.

In one aspect, the third reagent combination comprises a buffer (such as PBS) and a third master mix comprising e.g. EDTA, DTNB, $H_2O$ and a substrate NADPH for a GSH-specific enzyme, such as glutathione reductase.

In one aspect, the kit comprises an alcohol solution for preparing an extract of the biological sample for determining amounts of NAD+, NADP+, NADH, NADPH, NAD+/NADH ratio, NADPH/NADP+ ratio, NAD pool, and/or NADP pool. The alcohol solution can comprise e.g. ethanol, methanol and/or isopropanol and water; or the alcohol solution can be e.g. an ethanol, methanol or isopropanol solution. In one embodiment, the alcohol concentration of the alcohol solution is about 30-80%, 40-70%, 40-60%, 40-50%, 50-70%, 50-60%, 50% or 60%.

In one aspect of the method or kit of the present invention, concentrations of NAD+ and NADH are measured separately, NADP+ and NADPH are measured separately, concentration of GSH and GSSG is measured as pool of GSH, and/or concentration of GSSG is measured separately. In one aspect, the pool of NAD+ and NADH concentrations is measured as one entity in one plate and/or the pool of NADP+ and NADPH concentrations is measured as one entity in one plate. In one aspect, the method or kit comprises two or more multi-well plates for measuring concentrations of NAD+ and NADH separately; and/or two or more multi-well plates for measuring concentrations of NADP+ and NADPH separately. In one aspect, the method or kit comprises one or more multi-well plates for measuring concentrations of NAD pool, and/or one or more multi-well plates for measuring concentrations of. NADP pool. In one aspect, the method or kit comprises one or more multi-well plates for measuring concentrations of GSH and/or GSSG (e.g. GSSG and GSH simultaneously in one plate and/or GSSG separately in one plate) (See e.g. FIG. 1).

For example, Kit no 1 can comprise reagents for measuring concentrations of NAD+ and NADH e.g. in separate plates, or Method no 1 can measure concentrations of NAD+ and NADH e.g. in separate plates. For example, Kit no 2 can comprise reagents for measuring concentrations of NADP+ and NADPH e.g. in separate plates, or Method no 2 can measure concentrations of NADP+ and NADPH e.g. in separate plates. For example, Kit no 3 can comprise reagents for measuring concentrations of GSSG and GSH pool and GSSG e.g. in separate plates, or Method no 3 can measure concentrations of GSSG and GSH, and GSSG e.g. in separate plates. For example, Kit no 4 can comprise reagents for measuring concentrations of NAD+ and NADP+ e.g. in separate plates, and NADH and NADPH e.g. in separate plates; or Method no 4 can measure concentrations of NAD+ and NADP+ e.g. in separate plates, and NADH and NADPH e.g. in separate plates. For example, Kit no 5 can comprise reagents for measuring concentrations of NAD+ and NADP+ e.g. in separate plates, NADH and NADPH e.g. in separate plates, and GSSG and GSH pool and GSSG e.g. in separate plates; or Method no 5 can measure concentrations of NAD+ and NADP+ e.g. in separate plates, NADH and NADPH e.g. in separate plates, and GSSG and GSH pool and GSSG e.g. in separate plates. For example, Kit no 6 can comprise reagents for measuring concentration of a pool of NADP e.g. in the same plate; or Method no 6 can measure concentration of a pool of NADP e.g. in the same plate. For example, Kit no 7 can comprise reagents for measuring concentration of a pool of NAD e.g. in the same plate; or Method no 7 can measure concentration of a pool of NAD e.g. in the same plate. For example, Kit no 8 can comprise reagents for measuring concentration of a pool of NAD e.g. in the same plate, and a pool of NADP e.g. in the same plate; or Method no 8 can measure concentration of a pool of NAD e.g. in the same plate, and a pool of NADP e.g. in the same plate.

The assay of the present invention is based on utilizing an enzymatic cycling reaction e.g. with colorimetric detection and it can be adopted for a multi-well plate format. Detection mode of the method or kit of the present invention can be any conventional detection mode including but not limited to colorimetric, fluorescent, paramagnetic, electrochemical or label free detection mode. In one embodiment, NAD metabolites can be detected or analyzed by liquid chromatography and/or mass spectrometry (e.g. LC-MS and/or HPLC). In one embodiment, the method comprises measuring concentrations of NAD+, NADH, NADP+, NADPH, NAD pool, NADP pool, GSH and/or GSSG, or any combination thereof, by a colorimetric method. In one embodiment, the kit of the present invention is used for measuring concentrations of NAD+, NADH, NADP+, NADPH, NAD pool, NADP pool, GSH and/or GSSG, or any combination thereof, by a colorimetric method. As used herein, a colorimetric method refers to a method for determining the concentration of a chemical element or compound in a solution with the aid of a color reagent or chromogen. In one aspect, the amount or ratios of NAD+, NADP+, NADH, NADPH, NAD pool, and/or NADP pool are determined after an enzymatic reaction or reactions by measuring change in absorbance of chromogen at an appropriate wavelength relating to the reagents used, such as wavelength of 500-600 nm, 560-580 nm or 570-573 nm; and/or the amount or ratios of GSH and/or GSSG are determined after an enzymatic reaction by measuring change in absorbance of chromogen at an appropriate wavelength relating to the reagents used, such as wavelength of 350-480 nm, 400-420 nm or 410-415 nm. After measuring the absorbances, the concentrations of NAD metabolites in the extract can be determined by comparison of the assay response of the samples with assay response of the standards whose concentration is known. Then the concentrations of NAD metabolites in the extract can be normalized on the sample weight or protein amount of the sample or sample volume used for obtaining the extract. For example, one multi-well plate can accommodate e.g. maximum 40 samples, optionally together with standards, and measurement of concentrations of all four NAD metabolites from e.g. 40 samples can be accomplished in about 4-8 hours (e.g. 6 hours) by one person.

In one embodiment, NAD+ and NADH or NADP+ and NADPH metabolites from up to 18 samples can be measured on the same 96-well plate when each nucleotide from each sample is analyzed in duplicate.

In some aspects of the methods and kits of the invention, measured metabolite amount is normalized against e.g. the total protein content in the sample, tissue mass or the total amount of the sample e.g. the total volume in case of liquid biological sample such as blood. Normalization of metabolite amount e.g. on the protein content in the sample, tissue mass of the sample or blood volume can be introduced to the detection method or kit of the present invention. Indeed, in the method for measuring concentration of NAD metabolites or kit of the present invention several normalization options (including e.g., normalizing per volume of whole blood/cells or per protein amount (such as units (μM/L, pmol/mg) or per sample tissue mass (pmol/mg tissue)) suitable for research and clinical use can be utilized. In one aspect, the method of the present invention for measuring concentration of NAD metabolites from a sample comprises normalization of determined NAD+, NADH, NADP+, NADPH levels/amount and/or levels/amount of NAD pool and NADP pool against the total tissue mass of the used biological sample or the total protein amount of the biological sample or the whole blood volume of the biological sample, e.g., volume of the whole blood sample, and/or calculation of NAD+/NADH and/or NADPH/NADP+ ratios using normalized values of NAD metabolites.

In one aspect, the methods and kits of the invention include use of a standard curve based on known concentrations of commercially available standards used in the same assay together with analyzed samples. In one aspect of the methods and kits, determination of concentration of analyzed NAD metabolites is done by comparison of the assay response of a sample to that of the standards whose concentrations are known.

In one embodiment of the method or kit of the present invention, concentrations of standards used for preparation of the standard curve are validated by light spectroscopy. For example, in U.S. Pat. No. 6,287,796 B1 concentrations of standards used for standard curve are validated by light spectroscopy and diluted in a buffer assuring stability of standards. Therefore, this way of preparation of the standards for the assay does not account for possible losses of NAD metabolites during extraction from a sample due to, for example, non-optimal pH conditions during extraction, resulting in possible underestimation of measured metabolites. In one aspect of the present invention, the standards for the standard curve are prepared using the same conditions as the extraction of NAD metabolites from a sample, i.e., the standards are subjected to the same method steps. Subjecting the standards to the same treatment as samples allows control over any process-related variations, such as decrease of metabolites due to, e.g., degradation during a process. In one aspect of the present invention, the standards are provided at the beginning of the analysis at the step of extraction while in U.S. Pat. No. 6,287,796 B1 standards are provided at the end of analysis, e.g. in the assay.

Optionally, the method of the present invention may also comprise use of any suitable statistical methods known to a person skilled in the art. Accordingly, the sample may be analyzed in duplicate, triplicate or additional multiples to allow statistical analysis.

In one embodiment, the kit of the present invention is for the extraction and detection methods of the present invention.

With the extraction and detection methods, kit or tools of the present invention the presence, absence and/or amount of NAD+, NADH, NADP+, NADPH, NAD+/NADH ratio, NADPH/NADP+ ratio, NAD pool, NADP pool, GSH, GSSG and/or GSH/GSSG ratio can be determined from a sample.

The biological sample used for the method or kit of the present invention can be either a fresh or frozen sample. Due to the relatively high levels of NAD metabolites in cells and the sensitivity of the present method, the sample requirement for the method or kit of the present invention can be relatively small, e.g. 1-50 mg such as 10-20 mg of tissue, about 50000-about 2000000 cells such as about 500000-about 1000000 cells, and/or 50-500 μL such as 75-100 μL of the whole blood. In one aspect, all four NAD metabolites can be analyzed from a single drop of blood or a single sample of cells or tissue.

The methods or kits of the present invention are scalable and can be adopted for small and large sample number. Assay volumes for measuring NAD metabolites in the methods and kits of the present invention are also scalable and can be conducted in 1 mL optical cuvettes as well as scaled down to 200 μL volume of the well in 96-well plate or even lower. The sample can be any cell or tissue sample e.g. isolated cells, cultured cells, blood cells, whole blood, adipose tissue, or a tissue biopsy or surgical sample taken from a healthy or malignant tissue. Suitable biological samples also include but are not limited to plasma, serum, urine, tumor or cancer cells or tissue, liver tissue, liver cells, bone marrow, heart tissue, heart cells, muscle, muscle cells, brain tissue and/or brain cells and any surgically accessible sample type. Samples may be collected with any suitable method known to a person skilled in the art including but not limited to collecting blood, needle biopsy, aspiration, an open or closed biopsy procedure or a sample obtained during a surgery. The tissue can be fresh or frozen, and can include, e.g. frozen tissue sections.

The U.S. Pat. No. 6,287,796 B1 describes extraction protocol for NAD metabolites resulting in significant dilution of the initial whole blood sample of 36,75 times. This is, at least, because large volumes of concentrated alkali and acid are needed for efficient extraction of cellular metabolites and for removal proteins from the extract. Considerable dilution of initial blood sample during the extraction results in reducing concentration of NAD metabolites in the extract to the levels below detection limits of the assay. The improvements to the extraction and detection methods described herein allow analysis of much more concentrated extracts of samples. In one aspect of the method of the present invention, the initial sample of the whole blood is diluted 2-10 times, e.g., 2-8 times, e.g., 6-7 times. The low dilutions during extraction are particularly beneficial, e.g. when amounts of NAD metabolites are low in the sample. In one aspect, when amounts of NAD metabolites are high in the sample the obtained extract can be further diluted before the assay. In one aspect of the invention, the initial sample can be diluted e.g. 2-30 times, e.g. 6-20 times. This is particularly useful for measuring the amount of each NAD+, NADP+, NADH and NADPH individually or separately. Accordingly, because the method allows use of more concentrated sample(s), the method and the kit of the invention provide more sensitive and less complicated detection of the metabolites from the sample.

In one aspect, the kit further comprises instructions for carrying out extraction and/or detection methods of the present invention. E.g. said instructions may include instructions selected from the group consisting of instructions for carrying out the method for determining amounts of NAD metabolites, GSSG and/or GSH (e.g. for determining one or more from the group consisting of NAD+, NADH, NADP+, NADPH, NAD+/NADH ratio, NADPH/NADP+ ratio, NAD pool, NADP pool, GSH, GSSG and/or GSH/GSSG ratio), instructions for extracting NAD metabolites (and optionally GSSG and GSH) from a sample, instructions for diluting the samples to be studied, instructions for measuring an absorbance at a specific wavelength, instructions for the normalization of determined NAD+, NADH, NADP+ and/or NADPH levels on total protein amount or sample weight or whole blood volume, instructions for the calculation of NAD+/NADH and/or NADPH/NADP+ ratios, instructions for interpreting the results, instructions for carrying out the statistical analysis, and any combination of said instructions.

In one embodiment of the invention, the kit comprises reagents to determine at least the amount of NAD+, NADH, NADP+ and/or NADPH in a sample, and optionally one or more of the following group: a description of reference amount(s), e.g., a cut off value for determining that the level or amount of the metabolite is too "low" or the ratio is too "high"; a "normal" concentration range of the metabolites which has been determined from samples taken from a group of normal healthy subjects, for example healthy suitable subjects in certain age range or certain ethnicity, or certain genetic makeup for each NAD metabolite or a combination thereof; or one or more reference value ranges for disease conditions that can be identified by measuring specific metabolites or their ratios, such reference ranges having been identified using samples taken from subjects who are known to be affected by a disease condition for which the reference value range is to be provided; and/or instructions for carrying out a method for determining at least NAD+, NADH, NADP+ and/or NADPH of a sample of a subject.

In some embodiments, one or more control samples may be obtained from any control subject. Optionally positive and/or negative control samples of each NAD metabolite may be utilized in the present invention. Also, an extract from a random control sample with determined amounts of each NAD metabolite may optionally be present as quality control in the method or within the kit of the present invention.

In one embodiment of the invention, determination of the amount, absolute or relative, or ratios of NAD metabolites can be used as a biomarker for in vitro diagnosing a disease such as mitochondrial myopathy. In another embodiment, the kit of the present invention is for in vitro method.

In one embodiment of the invention, the subject is a human (e.g. a child, an adolescent or an adult), an animal (e.g. a mammal), fungus, micro-organism or plant. Suitable animals include but are not limited to mammals, birds, lizards, fish, worms and insects (such as flies). A subject can be in a need of determination of the amount or ratio of NAD metabolites, for example, for diagnosing a disease or a condition characterized by an abnormal amount of NAD+, NADP+, NADH, NADPH, and/or an abnormal NAD+/NADH ratio, NADPH/NADP+ ratio, or an abnormal quantity of NAD pool, and/or NADP pool, and optionally the amount of GSH, GSSG and/or GSH/GSSG ratio.

In one aspect, before classifying a subject as suitable for any method or kit of the present invention, the clinician may for example study any symptoms or assay any other disease markers, such as genetic markers of the subject to evaluate whether the clinician suspects a disease or condition that could be or symptoms of which could be a result of an abnormal amount or level or ratio of NAD metabolites. The clinician may suggest the method or kit of the present invention for determining NAD+, NADP+, NADH, NADPH, NAD+/NADH ratio, NADPH/NADP+ ratio, NAD pool, and/or NADP pool, and optionally GSH, GSSG and/or GSH/GSSG ratio, e.g. based on the results of other markers (such as deviating from the normal).

In one aspect, the method or kit of the present invention enables identifying subjects that are suitable targets of a treatment that allows improving the amount or ratio(s) of NAD metabolites and/or GSH, GSSG in the subject. An elevated or decreased level of at least one, two, three, four or more of NAD+, NADP+, NADH, NADPH, NAD+/NADH ratio, NADPH/NADP+ ratio, NAD pool, and NADP pool or GSH, GSSG in the sample compared to the levels of said metabolites in a reference value enables the clinician to find/diagnose the subjects who may benefit from a specific treatment directed to improving the levels or ratios of these metabolites thereby ameliorating a symptom or symptoms resulting from the imbalance of these metabolites. As used herein, the term "treatment" or "treating" refers to administration of at least one therapeutic agent to a subject for purposes which include any physiologically detectable amelioration or alleviation of disorders or symptoms related to the disorder in question or improvement of the NAD metabolite amount or balance as measured, e.g., using the methods or kits of the invention. Therapeutically effective amount of an agent refers to a safe and effective amount of the therapeutic agent.

The methods of the invention can also be used for monitoring the effect of a treatment on the levels or ratios of the NAD metabolites and/or GSH, GSSG, or optimizing the dosages of a treatment aimed at improving the amount and/or ratio of NAD metabolites or GSH, GSSG.

The methods or kits of the present invention can be used for diagnosing diseases as a biomarker for NAD-metabolic imbalance. In one aspect of the invention, the method for determining the amount or ratio of NAD metabolites and/or the extraction method further comprises diagnosing a disease or disorder, such as diabetes type I or II, muscle disease, fatty liver disease (non-alcoholic and acquired alcoholic), obesity, Parkinson's disease, Alzheimer's disease, other neurodegenerative diseases such as multiple sclerosis; lung disease, kidney disease, liver disease, thyroid disease, cardiac or cerebral stroke, chronic fatigue syndrome, ataxia disease, ocuar disease, mitochondrial disorder, metabolic disorder including inherited and non-inherited, anorexia, cachexia, viral or bacterial infection or related secondary disease such as immune reaction, endocrine disorders, nutrient deficiency, and cancer (such as a breast, colon, stomach, brain, pancreas, prostate, ovary, liver, lung or skin cancer, or leukemia), of children, teenagers or adults.

The present invention also relates to a method or a kit for diagnosing a disease or disorder, including diabetes type I or II, muscle disease, fatty liver disease (non-alcoholic and acquired alcoholic), obesity, Parkinson's disease, Alzheimer's disease, other neurodegenerative diseases such as multiple sclerosis; lung disease, kidney disease, liver disease, thyroid disease, cardiac or cerebral stroke, chronic fatigue syndrome, ataxia disease, ocular disease, mitochondrial disorder, metabolic disorder including inherited and non-inherited, anorexia, cachexia, viral or bacterial infection or related secondary disease such as immune reaction, endocrine disorders, nutrient deficiency, and cancer (such as a breast, colon, stomach, brain, pancreas, prostate, ovary, liver, lung or skin cancer, or leukemia), of children, teenagers or adults, wherein the method comprises determining the amount of NAD+, NADP+, NADH, NADPH, and/or the ratio of NAD+/NADH, NADPH/NADP+, the amount or level of NAD pool, and/or NADP pool and optionally GSH and/or GSSG from a sample of a subject.

As used herein the phrase "mitochondrial disorders" refers to a clinically heterogeneous group of disorders that arise as a result of either inherited or spontaneous mutations in mitochondrial DNA (mtDNA) or nuclear DNA (nDNA) which lead to altered functions of the proteins or RNA molecules that typically reside in mitochondria or are associated with mitochondrial function. Gene defects may be inherited maternally, or in an autosomal recessive, dominant or X-linked manner or occur sporadically in germ line or somatically in a specific tissue. Mitochondrial disorders may present at any age and may affect a single organ or multiple organs. Some individuals with a mutation in mtDNA or nDNA display clinical features falling within a clinical syndrome. However, disease phenotypes may greatly vary and thus many individuals do not fit into a specific clinical diagnosis. Because mitochondria perform many different functions in different tissues, they cause several different mitochondrial diseases. Symptoms of mitochondrial disorders may include but are not limited to one or more of the following: ptosis, external ophthalmoplegia, proximal or distal myopathy and exercise intolerance, muscle dystrophy or atrophy, cardiomyopathy, cardiac arrhythmia, sensorineural hearing loss, motor or sensory neuropathy, anaemia or bone marrow dysfunction, optic atrophy, retinopathy, cataracts, diabetes mellitus, exocrine pancreatic dysfunction, encephalopathy with atrophy or white matter disease or spongiosis, seizures, dementia, paranoia, depression, parkinsonism, migraine, kidney dysfunction, liver dysfunction, acute liver damage, fatty liver, gastro-intestinal dysfunction, anorexia, stroke-like episodes, strokes, severe developmental delays, inability to walk, talk, see, or digest food, ataxia, spasticity, early menopause, primary or secondary ovarian failure, testicular degeneration, sudden death, mid-and late pregnancy loss.

In one aspect of the invention, a mitochondrial disorder is a primary or secondary mitochondrial disorder. As used herein the phrase "a primary mitochondrial disorder" refers to a disorder that is caused by a mutation in a mitochondrial or nuclear genomic gene that encodes a protein that affects mitochondrial function. Since mitochondrial proteins are encoded by both nuclear or mitochondrial DNA, mutations leading to primary mitochondrial disorder can be nuclear and mitochondrial. As used herein the phrase "a secondary mitochondrial disorder" refers to a disorder that is caused by acquired mitochondrial abnormalities, including acquired genetic defects, which develop in response to pathologic processes involving mitochondria but not caused by mutations in mitochondrial proteins. Secondary mitochondrial disorders may also be due to nongenetic causes such as, but not limited to environmental factors, such as toxins, viruses or immune reactions, or a consequence of demyelination of nerve fibers. In one embodiment of the invention, mitochondrial disorders include but are not limited to one or more of the following: mitochondrial myopathy (muscle disease), mitochondrial cardiomyopathy, mitochondrial DNA maintenance disorders, mitochondrial DNA replication disease, mitochondrial DNA expression disease, mitochondrial DNA translation disorder, mitochondrial DNA deletion disease, mitochondrial DNA depletion syndrome, infantile-onset spinocerebellar ataxia (IOSCA), Leber's hereditary optic neuropathy (LHON), Pyruvate dehydrogenase complex deficiency (PDCD), Autosomal Dominant Optic Atrophy (ADOA), Kearns-Sayre syndrome (KSS), progressive external ophthalmoplegia (PEO), chronic progressive external ophthalmoplegia (CPEO), Mitochondrial myopathy (MMD), Carnitine palmitoyltransferase I (CPT I) Deficiency, CPT II Deficiency, mitochondrial encephalomyopathy with lactic acidosis and stroke-like episodes (MELAS), myoclonic epilepsy with ragged-red fibers (MERRF), neurogenic weakness with ataxia and retinitis pigmentosa (NARP), Leigh syndrome (LS), Luft Disease, mitochondrial recessive ataxia syndrome (MIRAS), Alpers-Huttenlocher syndrome (AHS), Barth Syndrome or LIC (Lethal Infantile Cardiomyopathy), beta-oxidation defects, carnitine-acyl-carnitine deficiency, carnitine deficiency, creatine deficiency syndromes, co-enzyme Q10 deficiency, combined or isolated respiratory chain deficiency (complex I deficiency, complex II deficiency, complex III deficiency, complex IV deficiency or cytochrome C-oxidase (COX) deficiency complex V deficiency, or combination of these), lactic acidosis, leukoencephalopathy with brain stem and spinal cord involvement and lactate elevation (LBSL)—leukodystrophy, long-chain acyl-CoA dehydrogenase deficiency (LCAD), long-chain 3-hydroxyacyl-CoA dehydrogenase deficiency (LCHAD), multiple acyl-CoA dehydrogenase deficiency (MAD) or glutaric aciduria type II, medium-chain acyl-CoA dehydrogenase deficiency (MCAD), mitochondrial cytopathy, mitochondrial encephalopathy, maternally inherited diabetes and deafness (MIDD), mitochondrial neurogastrointestinal disorder and encephalopathy (MNGIE), Pearson syndrome, pyruvate carboxylase deficiency, pyruvate dehydrogenase deficiency, mitochondrial polymerase gamma (POLG) defects such as Alpers Huttenlocher or Alpers disease, mitochondrial spinocerebellar ataxia epilepsy syndrome (M-SCA-E) sensory ataxic-neuropathy-dysarthria-ophthalmoparesis (SANDO), Parkinson-premature ovarian failure-neuropathy-mitochondrial myopathy; short-chain acyl-CoA dehydrogenase deficiency-encephalopathy and possibly liver disease or cardiomyopathy (SCHAD), very long-chain acyl-CoA dehydrogenase deficiency (VLCAD), Friedreich's ataxia, Parkinson's disease, Alzheimer disease, inclusion body myositis (IBM), fatty liver disease, ocular disease such as retinopathy, cataracts, optic atrophy and blindness.

In one aspect of the invention, the primary mitochondrial disorder is a dysfunction affecting the skeletal muscle, heart, central and/or peripheral nervous system, liver, kidney, pancreas, endocrine organs, intestine, lungs, reproductive organs and/or the sensory organ systems (such as eye and ear).

In one embodiment of the invention, the secondary mitochondrial disorder is an inclusion body myositis (IBM) or Parkinson's disease.

In one embodiment, an increased or decreased level/amount of NAD+, NADP+, NADH, NADPH, NAD+/NADH ratio, NADPH/NADP+ ratio, NAD pool, and/or NADP pool in the sample of the subject indicates manifestation or progression or need of treatment of a disorder, e.g. selected from the group consisting of diabetes type I or II, muscle disease, fatty liver disease (non-alcoholic and acquired alcoholic), obesity, Parkinson's disease, Alzheimer's disease, other neurodegenerative diseases such as multiple sclerosis; lung disease, kidney disease, liver disease, thyroid disease, cardiac or cerebral stroke, chronic fatigue syndrome, ataxia disease, ocular disease, mitochondrial disorder, metabolic disorder including inherited and non-inherited, anorexia, cachexia, viral or bacterial infection or related secondary disease such as immune reaction, endocrine disorders, nutrient deficiency, and cancer (such as a breast, colon, stomach, brain, pancreas, prostate, ovary, liver, lung or skin cancer, or leukemia), of children, teenagers or adults. In one embodiment, an increased or decreased level/amount of NAD+, NADP+, NADH, NADPH, NAD+/NADH ratio, NADPH/NADP+ ratio, NAD pool, and/or NADP pool in the sample of the subject indicates manifestation or progression or need of treatment of a disorder, e.g. selected from the group consisting of diabetes type I or II, Parkinson's disease, Alzheimer's disease, muscle disease such as PEO or MMD, chronic fatigue syndrome, mitochondrial disorder, such as MIRAS or MBD, and cancer such as a breast, colon, stomach, brain, pancreas, prostate, ovary, liver, lung or skin cancer (such as melanoma), or acute and chronic leukemia, of children, teenagers or adults. A decreased or increased level of NAD+, NADP+, NADH, NADPH, NAD+/NADH ratio, NADPH/NADP+ ratio, NAD pool, and/or NADP pool in the sample compared to the corresponding level in a control sample enables the clinician to e.g. make a diagnosis, select the subject for further examinations, or optimize or follow-up a specific treatment for the subject or progression of a disease.

In one aspect of the methods of the invention, one or more levels of NAD+, NADP+, NADH, NADPH, NAD+/NADH ratio, NADPH/NADP+ ratio, NAD pool, and/or NADP pool of the sample are compared to the corresponding levels of a control sample; or one or more levels of NAD+, NADP+, NADH, NADPH, NAD+/NADH ratio, NADPH/NADP+ ratio, NAD pool, and/or NADP pool of the sample are compared to the corresponding normal levels determined from a set of controls. Indeed, one or more NAD metabolites (e.g. a combination of all four NAD metabolites) can be used as disease biomarkers.

In one aspect, the method for determining a specific disease, in addition to NAD metabolites, may further comprise detection of other metabolites and/or proteins whose concentrations are known to change in a specific disease. Combined biomarkers provide higher sensitivity and specificity of diagnostic tools. In one embodiment of the kit for determining a specific disease, in addition to NAD metabolites, the kit further comprises tools for determining one or more further biomarkers in the sample of the subject.

In one embodiment, the invention further provides an extract comprising cellular metabolites produced by the extraction methods of the present invention. In one aspect, the extract is a frozen extract. In one aspect, the extract is made from healthy subjects. In one aspect, the extract is made from subjects who fall within a specific age range, such as children, adolescents or adults, or subjects over, for example, 50 years, or over 65 years. In some aspect, the extract can be an extract from subjects representing a genetic or clinical phenotype, such as subjects who all have one or more known shared genetic variation, or subjects who have been diagnosed as having a shared clinical symptom or group of symptoms. In some aspect, the extract can be used as a control sample in the methods or kits of the invention.

In one aspect, the invention further provides a method for measuring the amount of an intracellular metabolite in a tissue sample comprising:

a. extracting a mixture of intracellular metabolites from the tissue sample in the presence of a heated alcohol solution thereby obtaining an extract comprising the mixture of intracellular metabolites;
b. dividing the extract into at least a first and a second aliquot;
c. subjecting the first aliquot to acidic conditions to obtain an acid-treated fraction; and/or
d. subjecting the second aliquot to alkaline conditions to obtain an alkaline-treated fraction;
e. subjecting at least one aliquot of the acid-treated fraction, in the presence of non-ionic detergent, to a cycling process comprising two or more cycles of transferring an electron from a reduced intracellular metabolite to an electron acceptor dye molecule to produce a change in an absorbance of the electron acceptor dye molecule and measuring the change in the absorbance of the electron acceptor dye molecule, and comparing the change in the absorbance to a standard to measure the amount of the oxidized intracellular metabolite; and/or
f. subjecting at least one aliquot of the alkaline-treated fraction, in the presence of non-ionic detergent, to a cycling process comprising two or more cycles of transferring an electron from a reduced intracellular metabolite to an electron acceptor dye molecule to produce a change in an absorbance of the electron acceptor dye molecule and measuring the change in the absorbance of the electron acceptor dye molecule, and comparing the change in the absorbance to a standard to measure the amount of the reduced intracellular metabolite.

In another aspect, the invention provides a method for preparing a cellular extract from a tissue sample, the method comprising the steps of a. incubating the tissue sample in a heated alcohol solution;
b. cooling the heated alcohol solution from step (a) thereby obtaining a tissue homogenate; and
c. separating solids from the tissue homogenate thereby obtaining the cellular extract.

In some aspects, the methods of the invention further comprise freezing the cellular extract, for example at −80° C., and in some aspects, the frozen cellular extracts are stored.

In some aspects of the methods of the invention, the step of incubating is performed between 30 seconds and 5 minutes, for example 1-3 minutes.

In some aspects of the methods of the invention, the cellular extract comprises pyridine nucleotides, including NAD+, NADP+, NADH and NADPH, and further comprises reduced and oxidized forms of glutathione GSH and GSSG.

In some aspects of the methods of the invention, the methods further comprise determining the amount of NAD+, NADP+, NADH and NADPH, and/or reduced and oxidized forms of glutathione GSH and GSSG.

The invention also provides a method for releasing cellular low molecular weight metabolites into a cellular extract, the method comprising a. exposing the tissue sample to heated alcohol solution;
b. cooling the alcohol solution from step (a) thereby obtaining a tissue homogenate; and
c. separating solids from the tissue homogenate thereby obtaining the cellular extract comprising cellular low molecular weight metabolites.

The invention also provides a method for obtaining oxidized and/or reduced pyridine nucleotides from a cellular extract, the method comprising the steps of a. making a cellular extract comprising exposing the tissue sample to a heated alcohol solution, cooling the solution, and removing the solids from the solution to
b. dividing the cellular extract into first and second aliquot;
c. contacting the first aliquot with a strong acid thereby obtaining oxidized pyridine nucleotides from the cellular extract; and/or
d. contacting the second aliquot with a strong alkaline thereby obtaining reduced pyridine nucleotides from the cellular extract.

The invention further provides a method of measuring amount of a pyridine nucleotide in a cellular extract, the method comprising contacting the cellular extract with a reaction mixture comprising an electron carrier, a chromogen, a non-ionic detergent, and an enzyme, optionally stopping the reaction, measuring the amount of the chromogen and comparing the amount of the chromogen to a standard thereby measuring the amount of the pyridine nucleotide. In some aspects of the method, the pyridine nucleotide comprises NAD+, NADH, NADP+ and/or NADPH and any combination thereof.

The invention still further provides a method for detecting the amount one or more cellular metabolite in a tissue sample, and optionally further measuring the amount of the one or more cellular metabolite and/or one or more ratio between the cellular metabolites in the tissue sample, the method comprising steps A; B or C, and optionally D; and/or E:

A) preparing a cellular extract from a tissue sample, the method comprising the steps of
   a. exposing the tissue sample to heated alcohol solution;
   b. cooling the alcohol solution with the tissue sample after the heat treatment thereby obtaining a tissue homogenate comprising a mixture of the cellular extract and solids; and
   c. removing the solids from the tissue homogenate to obtain the cellular extract;

B) detecting in the cellular extract the amount of at least one low molecular weight metabolite, comprising NAD+, NADP+, NADH and/or NADPH, wherein the detecting comprises
   i) contacting a first part of the cellular extract with a strong acid to stabilize NAD+ and NADP+ and to eliminate NADH and NADPH in the first part of the extract, and/or
   contacting a second part of the extract with a strong alkali to stabilize NADH and NADPH and to eliminate NAD+ and NADP+ in the second part of the extract; and carrying out one or more of the following steps B ii)-v) for the detection of the NAD+, NADP+, NADH and/or NADPH,
   ii) detecting the amount of NAD+, wherein the detecting comprises contacting an aliquot of the first part of the extract with a first NAD-specific enzyme in the presence of a detection system comprising an electron carrier, a chromogen and a non-ionic detergent to obtain an enzymatic reaction for detecting NAD+, and/or
   iii) detecting the amount of NADH, wherein the detecting comprises contacting an aliquot of the second part of the extract with a first NAD-specific enzyme in the presence of a detection system comprising an electron carrier, a chromogen and a non-ionic detergent to obtain an enzymatic reaction for detecting NADH, and/or
   iv) detecting the amount of NADP+, wherein the detecting comprises contacting an aliquot of the first part of the extract with a second NADP-specific enzyme in the presence of a detection system comprising an electron carrier, a chromogen and a non-ionic detergent to obtain an enzymatic reaction for detecting NADP+, and/or
   v) detecting the amount of NADPH, wherein the detecting comprises contacting an aliquot of the second part of the extract with a second NADP-specific enzyme in the presence of a detection system comprising an electron carrier, a chromogen and a non-ionic detergent to obtain an enzymatic reaction for detecting NADPH; and/or C) detecting the amount of NAD pool (NAD+ and NADH together) and NADP pool (NADP+ and NADPH together), wherein the detecting comprises
i) contacting a third part of the cellular extract with a first NAD-specific enzyme in the presence of a detection system comprising an electron carrier, chromogen and non-ionic detergent to obtain an enzymatic reaction for detecting the amount of NAD pool, and/or
   ii) contacting a fourth part of the cellular extract with a second NADP-specific enzyme in the presence of a detection system comprising an electron carrier, chromogen and non-ionic detergent to obtain an enzymatic reaction for detecting the amount of NADP pool; and optionally D) determining the amount of NAD+, NADP+, NADH, NADPH, and/or the ratio of NAD+/NADH, the ratio of NADPH/NADP+, the amount of the NAD pool, and/or the amount of the NADP pool, the measuring comprising comparing one or more of the detected amounts of the cellular metabolite to a standard with known concentration; and/or E) detecting the amount of GSH and/or GSSG in the cellular extract, the detecting comprising
   (i) detecting the amount of GSSG comprising removing GSH from a fifth part of the cellular extract by a chemical modification and contacting GSSG of the fifth part of the extract with a GSH-specific enzyme, such as glutathione reductase in the presence of added NADPH and a reporter, and optionally measuring the amount of GSSG comprising comparing the detected amount to a standard, and/or
   ii) detecting the amount of GSH and GSSG together comprising contacting GSH and GSSG of a sixth part of the cellular extract with a GSH-specific enzyme, such as glutathione reductase in the presence of added NADPH and a reporter, and optionally measuring the amount of GSH and GSSG comprising comparing the detected amount to a standard.

It will be obvious to a person skilled in the art that, as the technology advances, the inventive concept can be implemented in various ways. The invention and its embodiments are not limited to the examples described below but may vary within the scope of the claims.

EXAMPLES

Example 1

Extraction

Fresh or frozen samples are added into pre-heated ethanol solution (e.g. a temperature of at least about 45-80° C.) followed by short incubation in the heated ethanol solution, resulting in: 1) cell lysis; 2) unfolding of proteins in a sample; and 3) release of metabolites into the ethanol solution. Precipitation of denatured proteins is induced by incubation of the homogenate on ice followed by centrifugation. The supernatant from the centrifugation step comprises metabolites including NAD+, NADP+, NADH, NADPH, GSSG and GSH. Measurement of metabolites can be performed on the same day or extraction or extracts can be snap-frozen and stored at −80° C. before subjecting them to the assay.

Detection

To measure separately oxidized and reduced forms of NAD metabolites the extract is split onto two parts. One part is treated with alkaline, such as NaOH followed by short heating step at temperatures of at least about 50°-80° C. to stabilize NADH and NADPH and destroy NAD+ and NADP+; the other part is treated with acid, such as HCL at ambient temperatures of at least 22°-26° C. to stabilize NAD+ and NADP+ and eliminate NADH and NADPH from the assay. Detection of NAD metabolites after stabilization step are done within the same day.

The amount of NAD+, NADH, NADP+ and NADPH are different in a sample by nature of NAD metabolism with prevalence of one NAD metabolite over the other. Therefore, to allow more accurate analysis of some of the NAD metabolites, an aliquot from the extract with stabilized NAD metabolite can be further diluted before analysis in order to fit into the standard curve.

After extraction of the metabolites, the extract contains large amount of low molecular weight metabolites, which collectively are referred to as a "matrix". Some components of this matrix may non-specifically interact with PES and MTT in the reaction mixture and contribute to unspecific color development during the reaction conditions. To correct for unspecific reactions, typically at least 2 reactions, such as at least two wells on a multi-well plate are performed without addition of the enzyme, thus allowing the method to control for the unspecific color formation.

A typical time for the enzymatic reactions is between 5-15 min or 5-10 min. Accordingly, the method provides a very rapid, about 5-15 or about 5-10 minutes assay for the metabolites.

Normalization

For normalization of the pyridine nucleotide levels the total protein amount or total weight of the tissue sample or volume in case of biological fluid can be used.

Samples

One sample and one aliquot of the extract made from the sample is sufficient for the measurement of all four NAD metabolites.

For analysis of NAD metabolites in the whole blood, a sample is collected into a tube with the anticoagulant. Both heparin and EDTA collection tubes (BD K2E Vacutainer) can be used. The assay of four metabolites requires about 100 μL of the whole blood. The assay can be performed using the fresh whole blood sample or an aliquot and the sample can be frozen as soon as possible after collection for a later use. The frozen aliquots should be stored at −80° C. The frozen samples can later be subjected to the extraction methods. The amount of NAD metabolites measured from fresh and frozen blood are not exactly the same due to the freeze-thaw process and this should be taken into consideration when selecting controls for, for example, diagnostic purposes.

The following method steps are carried out in one embodiment of the invention:

I. Metabolite Extraction

PROTOCOL:

1) Frozen liquid samples were thawed on ice-water bath for 15-20 min prior to the extraction. If fresh samples were used, they were cooled on ice prior to the extraction method. Solid tissue sample types were kept frozen prior extraction. Solid tissue sample could by tissue samples collected from laboratory animals, for example from mice, or biopsy samples taken from human patients.

2a) When a liquid sample was used, an aliquot of 500 μL of 60% EtOH was heated to +50-+80° C.

2b) When a solid tissue sample was used, an aliquot of 50% EtOH containing 0.2% Triton™M X-100 to get final concentration 20 mg of tissue per mL was heated to +50-+60° C.

2c) When cell pellet was used-aliquot of 300 μL of 50% EtOH containing 0.2% Triton™M X-100 was heated to +50° C.-+60° C.

3a) When a liquid sample was used, 100 μL of the sample was directly added into pre-heated EtOH solution, mixed quickly and efficiently by pipetting.

3b) When a solid tissue sample was used, a frozen piece of the sample was placed into pre-heated EtOH solution and homogenized using one of the conventional ways.

3c) When a cell pellet was used, the pre-heated EtOH solution was added on the cell pellet and the cell pellet was resuspended by pipetting.

4) Obtained homogenate from any of the above-exemplified tissue samples was incubated in the hot EtOH solution at +50-+80° C. for 1 min.

5) After the 1 min incubation in step (4), the resulting homogenate was cooled on ice-water bath.

6) Denatured proteins were removed from the homogenate by centrifugation at 20 000 x g, 10 min at +4° C.The supernatant obtained after the centrifugation contains all four NAD metabolites and a large number of other metabolites. This extract can be used for detection of NAD metabolites the same day or it can be stored frozen at −80° C. and restored before further analysis. This extract also can be used in mass spectroscopy analysis of other cellular metabolites.

7) When sample had high amount of lipids then extraction solution of 70% EtOH with 0.2% Triton™M X-100 was used.

II. Elimination of NAD+/NADP+ from the Extract for Measurement of NADH/NADPH, Elimination of NADH/NADPH from the Extract for Measurement of NAD+/NADP+

Protocol:

1) Two aliquots of 150 μL/each of the extract comprising cellular metabolites were prepared at room temperature—2×150 μL. The first aliquot was for measuring NAD+/NADP+ and the second aliquot was for measuring NADH/NADPH.

2) 100 μL of 0.1M HCl was mixed into 150 μL of the first extract aliquot dedicated for NAD+/NADP+ measurement, and incubated for 5 min at temperature of 22°-26° C., then stored at +4° C. until performing the assay on the same day.

3) 100 μL of 0.1M NaOH was mixed into 150 μL of the second aliquot of the extract dedicated for NADH/NADPH measurement, and incubated for 1 min at +60-+80° C., cooled on ice-water bath for 5 min, then stored at +4° C. protected from light until assay on the same day.

4) The final dilution of the whole blood in the stored extract with stabilized NAD+/NADP+ or with stabilized NADH/NADPH was 10 times.

III. Preparation of Standards of NAD Metabolites

General Notes

It is preferable to use commercially available sodium salt hydrates of NAD+, NADH, NADP+ and/or NADPH of highest purity as standards. It is preferable to store the standards as powders, and desiccated at −20° C. When preparing the standards for the assay, it is preferable to prepare stock solutions of each standard with concentration 1 mM. Use 0.1 M NaOH to prepare 1 mM of NADH/NADPH and 0.1M HCL to prepare 1 mM NAD+/NADP+. Use light absorbance properties of NAD molecules to prepare 1 mM standards. Extinction coefficient for NADH/NADPH is 6.22 mM×cm$^{-1}$ at 340 nm, for NAD+/NADP+ is 18 mM×cm$^{-1}$ at 260 nm ("Specifications and Criteria for Biochemical Compounds, 3rd ed., National Academy of Sciences (Washington, DC: 1972), p. 87). It is possible to store prepared 1 mM stocks at −80° C. for up to about one-two months. Each aliquot of 1 mM standard stock should be used only one time. The solutions should not be refrozen.

Example Protocol:

1) 50 μM stock of each standard nucleotide was prepared by adding 25 μL of 1 mM stock into 475 μL of 1×PBS to reproduce physiological conditions.
2) 100 μL of the standards for the assay were prepared according to the Table 1. These volumes were not final, they correspond to volume of the blood sample used for extraction. These 100 μL underwent the same treatment as samples and at the end were diluted 10 times. Final concentration of the standard after dilution of prepared 100 μL aliquot is given in the left column of Table 1.

TABLE 1

| Concentration of the standard solution in final 1 mL (nM) | Preparation: Volume (μL) of 50 μM stock | Volume (μL) 1× PBS |
|---|---|---|
| 125 | 2.5 | 97.5 |
| 250 | 5 | 95 |
| 500 | 10 | 90 |
| 1000 | 20 | 80 |
| 2000 | 40 | 60 |
| 3000 | 60 | 40 |

3) Aliquots of 500 μL of 60% EtOH were heated at +50-+80° C. for 2 min.
4) Prepared 100 μL standard solutions were added into pre-heated EtOH solution, mixed by pipetting and incubated at +50-+80° C. for 1 min.
5) After step (4), the samples were cooled on ice-water bath for 5 min, and transferred to room temperature.
6) 400 μL of 0.1 M NaOH was added into each NADH and NADPH standard mixture, the mixtures were vortexed, heated at +50-+80° C. for 1 min, cooled on ice-water bath for 5 min, transferred to +4° C. and protected from light until the assay was performed on the same day.
7) 400 μL of 0.1 M HCl was added into each NAD+ and NADP+ standard, vortexed, incubated for 5 min at temperature of 22-26° C. and transferred to +4° C. and protected from light until the assay.
8) Final volume of each standard became 1 mL, with final concentration indicated in the left column of the Table 1.

IV. NAD+/NADH Colorimetric Assay

Note: Protocol below is for assay in 96-well plate format. Protocol is the same for NAD+and NADH measurement. Each sample can be analyzed in duplicates or triplicates or more.

1) Before pipetting samples and standards onto plate we prepared A) two aliquots of 18 mL (for detection system) and 2.5 mL (for Blanks) of Master mix per one 96-well plate containing 110 mM Bicine-NaOH, pH 8.0, 4.5 mM EDTA, 0.6 M EtOH, 0.5 mM MTT, 2 mM PES, 0.2% TritonTM X-100 and kept it at room temperature protected from light for maximum one hour before the assay; B) 40 μL of Alcohol dehydrogenase from Baker's yeast with concentration of 5000 U/mL in 0.1 M Bicine-NaOH, pH 8.0 per one 96-well plate.
2) First, 20 μL of each standard was pipetted in duplicates on the plate starting from 0 point to produce standard curve in the assay. As zero point 0.04 M NaOH or 0.04 M HCl was used.
3) Standard of 500 nM was also pipetted separately in duplicate to be analyzed without added enzyme to produce Blank for all the standards to correct for possible unspecific interaction with detection system.
4) Each stabilized sample was pipetted in duplicates or triplicates of 20 μL each.
5) Eight randomly selected samples were used to produce mean value of Blank for samples to correct for unspecific interaction with detection system. For this 20 μL of each selected sample were pipetted separately in one replicate.
6) Next, 18 mL aliquot of Master mix was mixed with 40 μL of enzyme and 190 μL of this complete detection system was added to all the wells except for Blanks.
7) Then 190 μL of Master mix without added enzyme from 2.5 mL Master mix aliquot was pipetted to each of the Blanks.
8) Plate was covered with a foil and incubated at room temperature for 5-10 min.
9) Reaction was stopped by addition of 10 μL of 11% SDS with mixing to all the wells including Blanks.
10) Absorbance was measured at 573 nm using a plate reader.

V. NADP+/NADPH Colorimetric Assay

Note: Protocol below is for assay in 96-well plate format. Protocol is the same for NADP+ and NADPH measurement. Each sample can be analyzed in duplicates or triplicates or more.

1) Before pipetting samples and standards onto plate we prepared A) two aliquots of 18 mL (for detection system) and 2.5 mL (for Blanks) of Master mix per one 96-well plate containing 110 mM Bicine-NaOH, pH 8.0, 4.5 mM EDTA, 3 mM glucose-6-phosphate (G6P), 0.5 mM MTT, 2 mM PES, 0.2% Triton™ M X-100 and kept it at room temperature protected from light for max one hour before the assay; B) 40 μL of Glucose-6-phosphate dehydrogenase from Baker's yeast of 250 U/mL in 0.1 M Bicine-NaOH, pH 8.0 per one 96-well plate.
2) First, 20 μL of each standard was pipetted in duplicates on the plate starting from 0 point to produce standard curve in the assay. As zero point 0.04 M NaOH or 0.04 M HCI was used.
3) Standard of 500 nM was also pipetted separately in duplicate to be analyzed without added enzyme to produce Blank for all the standards to correct for possible unspecific interaction with detection system.
4) Each stabilized sample was pipetted in duplicates or triplicates of 20 μL each.
5) Eight randomly selected samples were used to produce mean value of Blank for samples to correct for unspecific interaction with detection system. For this 20 μL of each selected sample were pipetted separately in one replicate.
6) Next, 18 mL aliquot of Master mix was mixed with 40 μL of enzyme and 190 μL of this complete detection system was added to all the wells except for Blanks.
7) Then 190 μL of Master mix without added enzyme from 2.5 mL Master mix aliquot was pipetted to each of the Blanks.

8) The plate was covered with a foil and incubated at room temperature for 5-10 min.
9) The reaction was stopped by injection of 10 μL of 11% SDS with mixing into all the wells including Blanks.
10) Absorbance was measured at 573 nm using plate reader.

VI. Protein Assay

Measurement of protein concentration can be done using one of commercially available Protein Assay kits. We used PIERCE BCA protein assay kit from Thermo Fisher Scientific. For measurement of protein concentration, the whole blood was diluted 200 times with distilled water before measurement. When there was a need to measure protein amount in the pellet obtained after homogenate centrifugation, pellet was solubilized in appropriate amount of 250 mM NaOH containing 1% SDS followed by sonication and subsequent 10-time dilution with 100 mM PBS, pH 7.5.

VII. Data Analysis and Normalization of the Metabolite Content for Blood Volume or Protein Concentration or Tissue Mass 1) Absorption values in all the standards were corrected with absorption of standards' Blank. Mean value for absorption of duplicate of each standard was calculated and a standard curve was constructed by applying linear regression fitting function.
2) Absorbance value for each sample was corrected for absorption of the mean of samples Blanks. Then mean absorbance level for duplicate or triplicate of each sample was calculated, and concentration of nucleotide was calculated in the extract based on the standard curve.
3) The concentration of the analyzed metabolite was normalized per volume in case of blood sample accounting for the dilution during preparation of the extract or tissue mass or protein content in the homogenate.

Example 2: A Comparative Example

The blood sample from one control individual was used and treated either with the method and conditions presented in U.S. Pat. No. 6,287,796 B1 or with the method of the present invention and conditions presented in example 1.

Due to a lack of information about effect of chemicals used in the extraction method of U.S. Pat. No. 6,287,796 B1 on enzymatic reaction, we used the same enzyme (G6P-dehydrogenase) for the method of U.S. Pat. No. 6,287,796 B1 and the method of the present invention.

Figure 3:
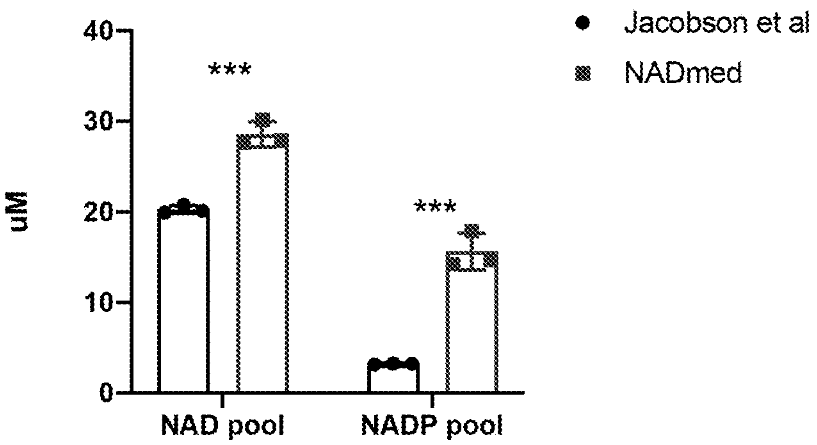
FIG. 3 shows results of the comparative example, wherein the same biological sample was used and treated either with the method and conditions presented in U.S. Pat. No. 6,287,796 B1 or with the method of the present invention and conditions presented in example 1. Very low levels of NADP pool were detected with the method of U.S. Pat. No. 6,287,796 B1. Higher detection levels of NADP pool with the method and kit of the present invention reveal better performance compared to the prior art method.
Figure 4A:
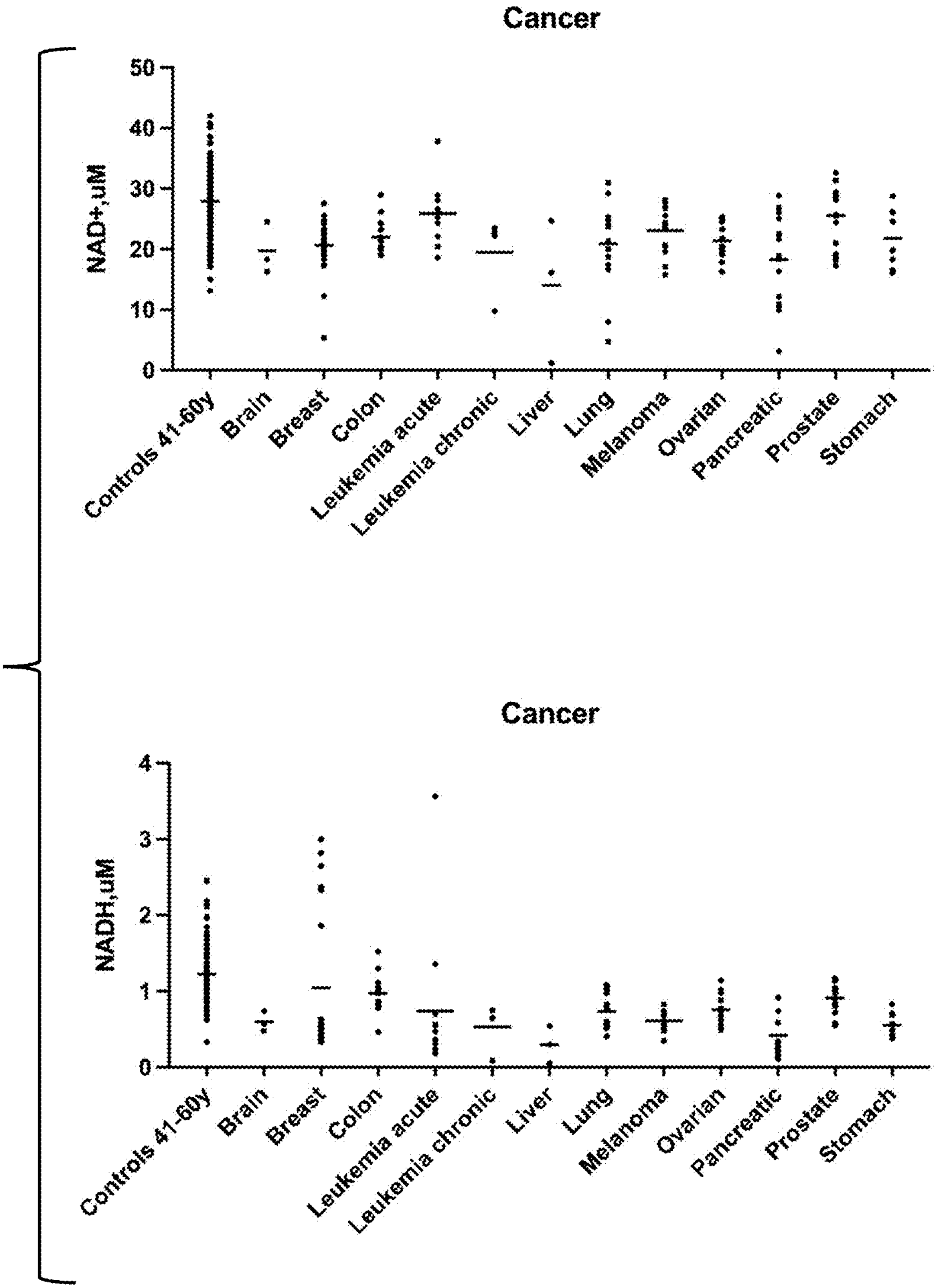
FIGS. 4A-4C show results of measuring the individual concentrations of pyridine nucleotides NAD+ and NADH (FIG. 4A), NADP+ and NADPH (FIG. 4B), and reduced and oxidized forms of glutathione GSH and GSSG (FIG. 4C) from blood samples of healthy controls and several cancer types using the present invention. Healthy controls (age 41-60 years, n=125), brain cancer (n=3), breast cancer (n=22), colon cancer (n=15), acute leukemia (n=12), chronic leukemia (n=4), liver cancer (n=3), lung cancer (n=15), melanoma (n=16), ovarian cancer (n=12), pancreatic cancer (n=15), prostate cancer (n=16) and stomach cancer (n=9). Source for the healthy controls was Finnish Red Cross Blood service BioBank, all pathology samples were from Auria BioBank (Turku).
Figure 4B:
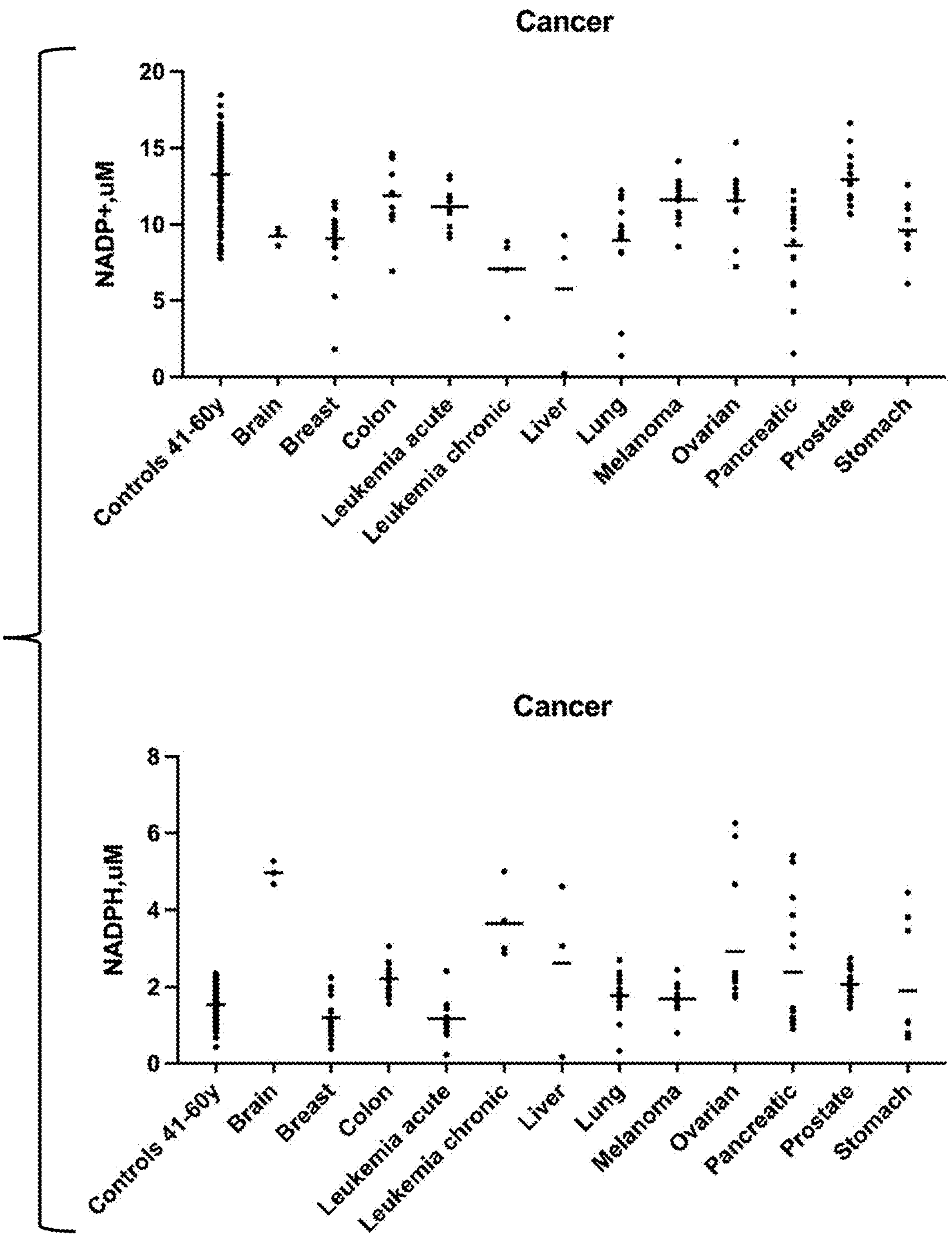
Figure 4C:
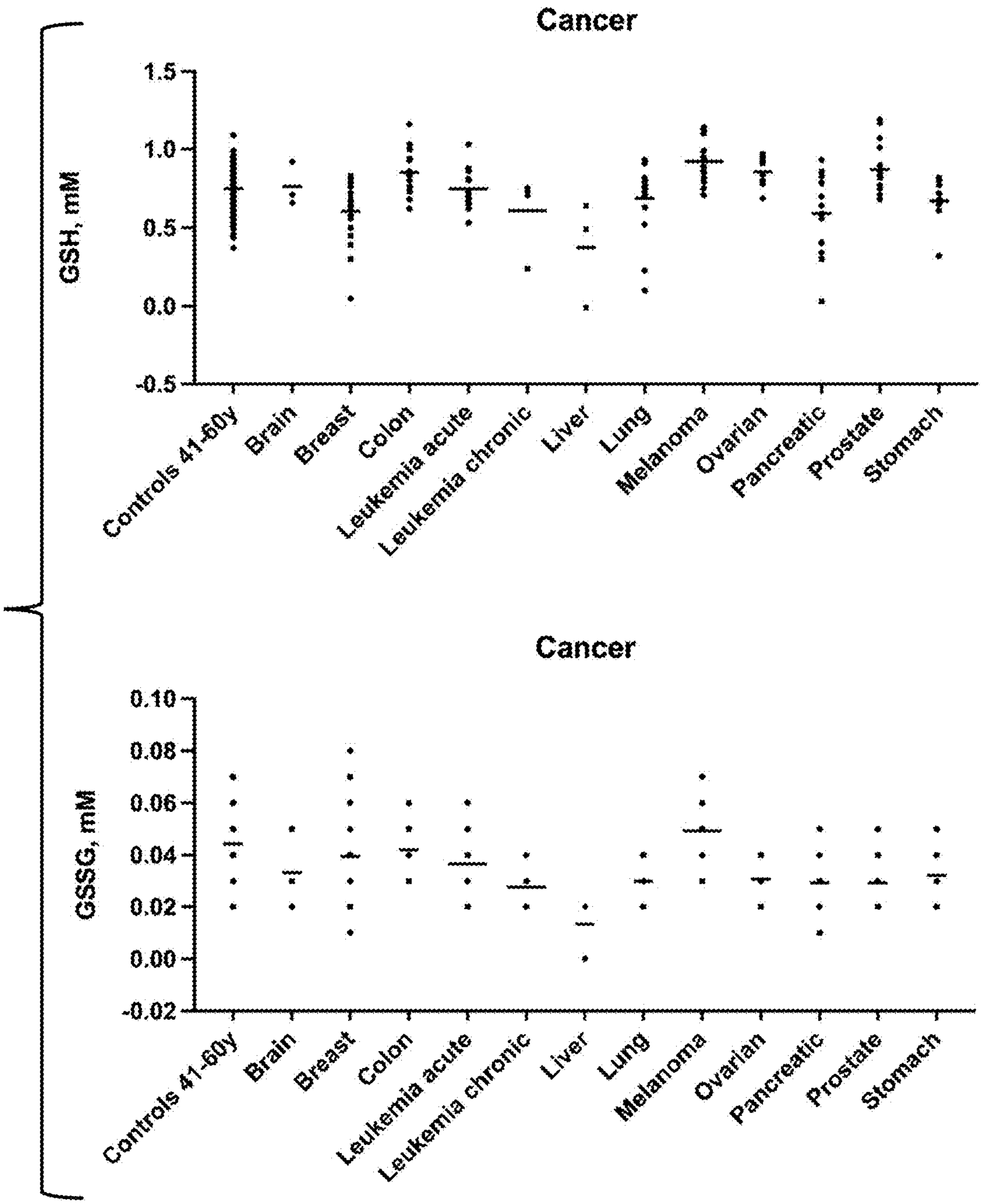
Figure 5A:
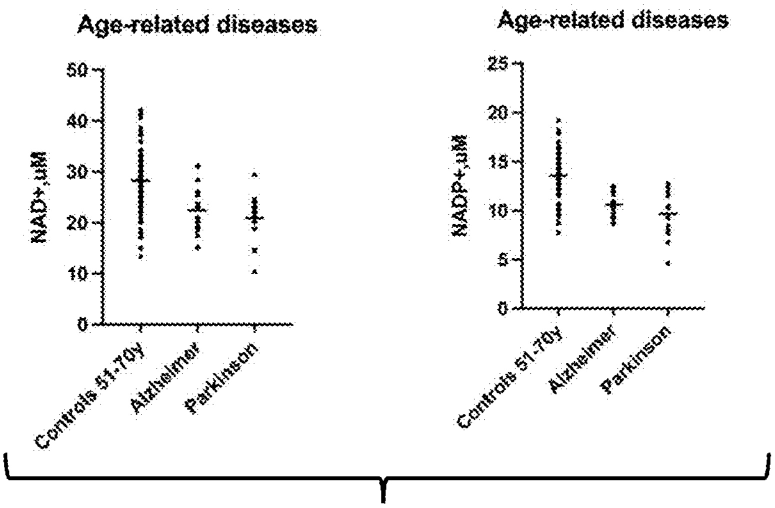
FIGS. 5A-5C show results of measuring the individual concentrations of pyridine nucleotides NAD+ and NADH (FIG. 5A), NADP+ and NADPH (FIG. 5B), and reduced and oxidized forms of glutathione GSH and GSSG (FIG. 5C) from blood samples of healthy controls and patients with age-related diseases e.g. Alzheimer's and Parkinson's disease using the present invention. Different levels of NAD+, NADH, NADP+, NADPH, GSH and GSSG are detected in each disease compared to healthy controls. Healthy controls (age 51-70 years, n=86), Alzheimer's disease (n=15) and Parkinson's disease (n=15). Sources for the samples are the same as described in FIGS. 4A-4C.
Figure 5B:
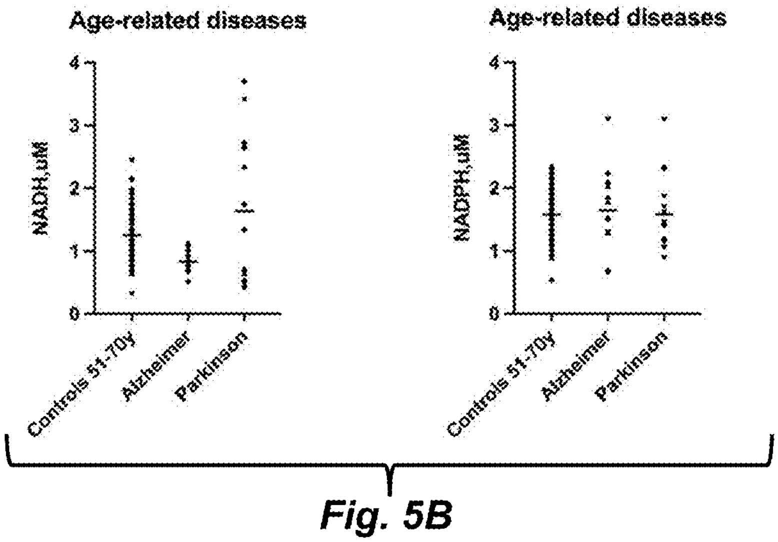
Figure 5C:
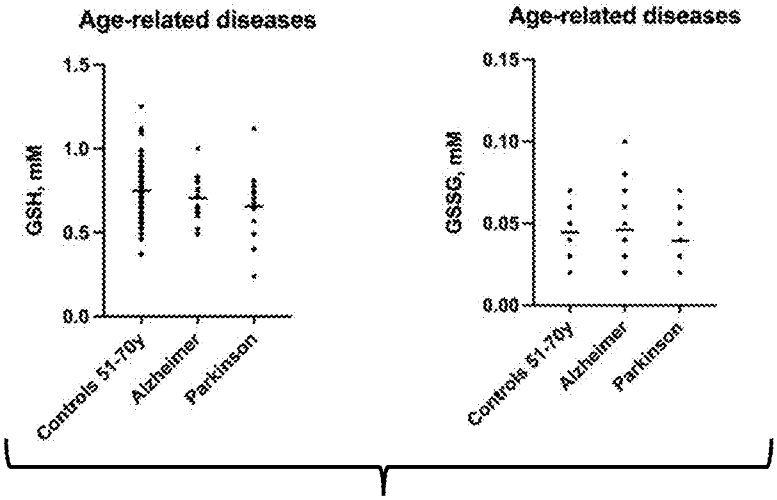
Figure 6A:
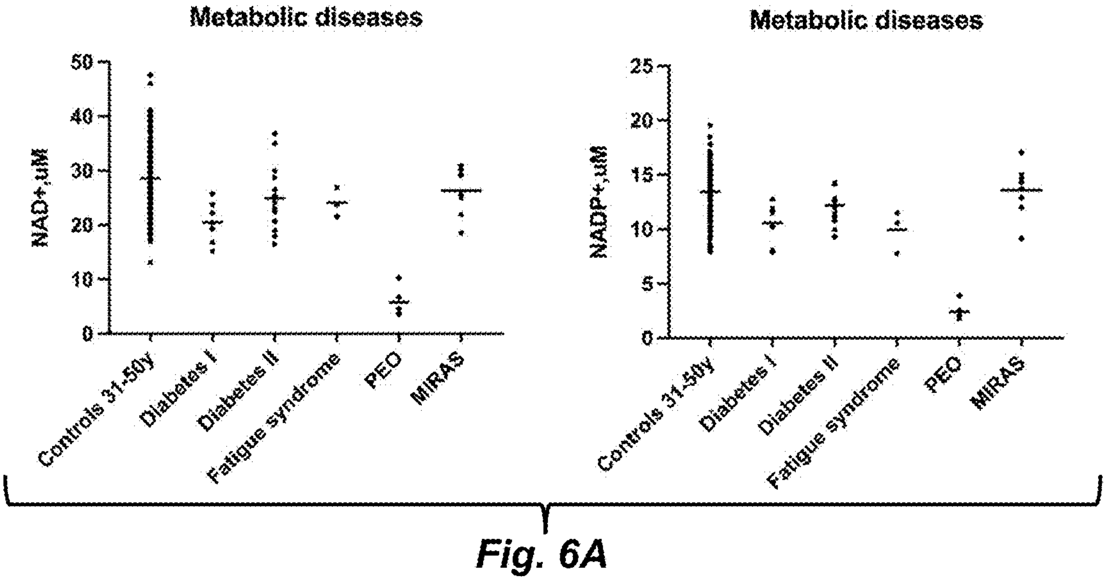
FIGS. 6A-6C show results of measuring the individual concentrations of pyridine nucleotides NAD+ and NADH (FIG. 6A), NADP+ and NADPH (FIG. 6B), and reduced and oxidized forms of glutathione GSH and GSSG (FIG. 6C) from blood samples of healthy controls and patients with metabolic diseases, e.g. Diabetes type I and II, chronic fatigue syndrome, mitochondrial muscle disease, and mitochondrial brain disease, using the present invention. Different levels of NAD+, NADH, NADP+, NADPH, GSH and GSSG are detected in each disease compared to healthy controls. Healthy controls (age 31-50 years, n=127), Diabetes type I (n=7), Diabetes type II (n=15), chronic fatigue syndrome (n=3), mitochondrial muscle disease (MMD, n=5) and mitochondrial brain disease (MBD, n=8). Sources for the samples are the same as described in FIGS. 4A-4C, except that MMD and MBD patients are from sample collection of Prof. Anu Wartiovaara laboratory.
Figure 6B:
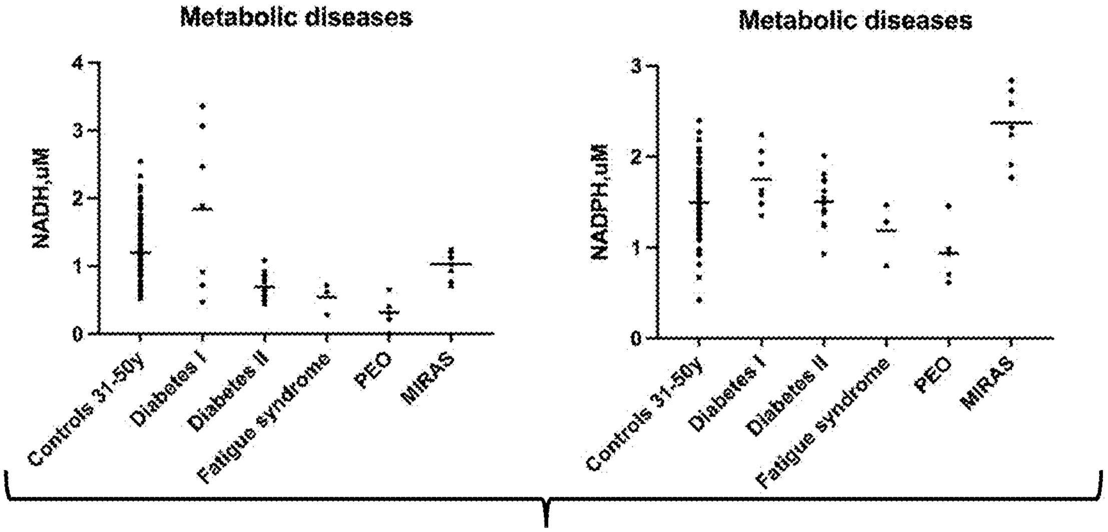
Figure 6C:
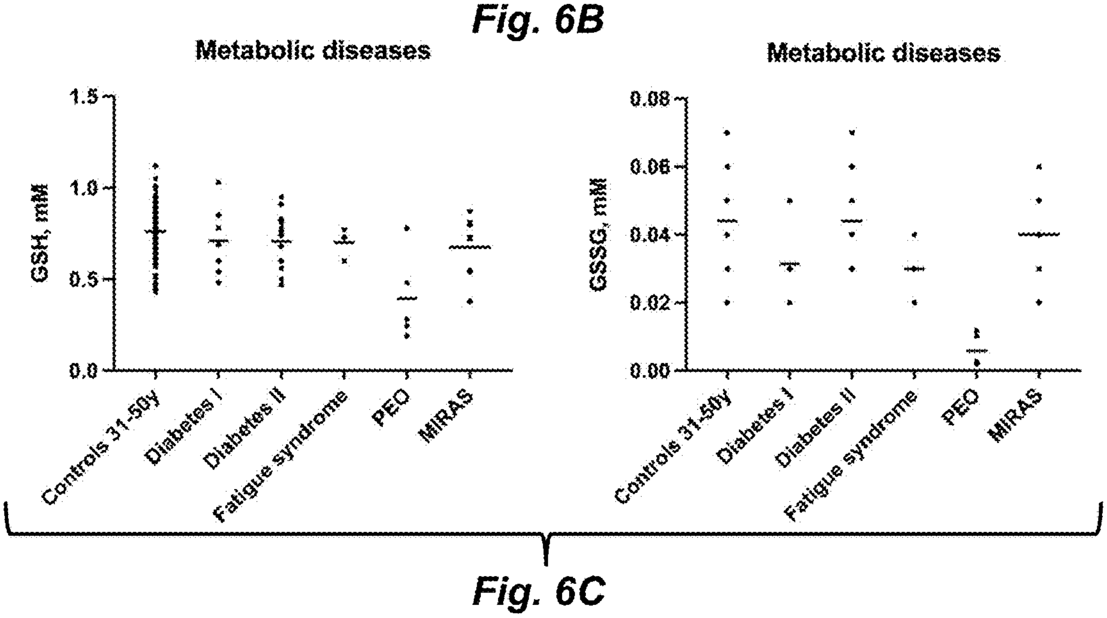
Figure 7A:
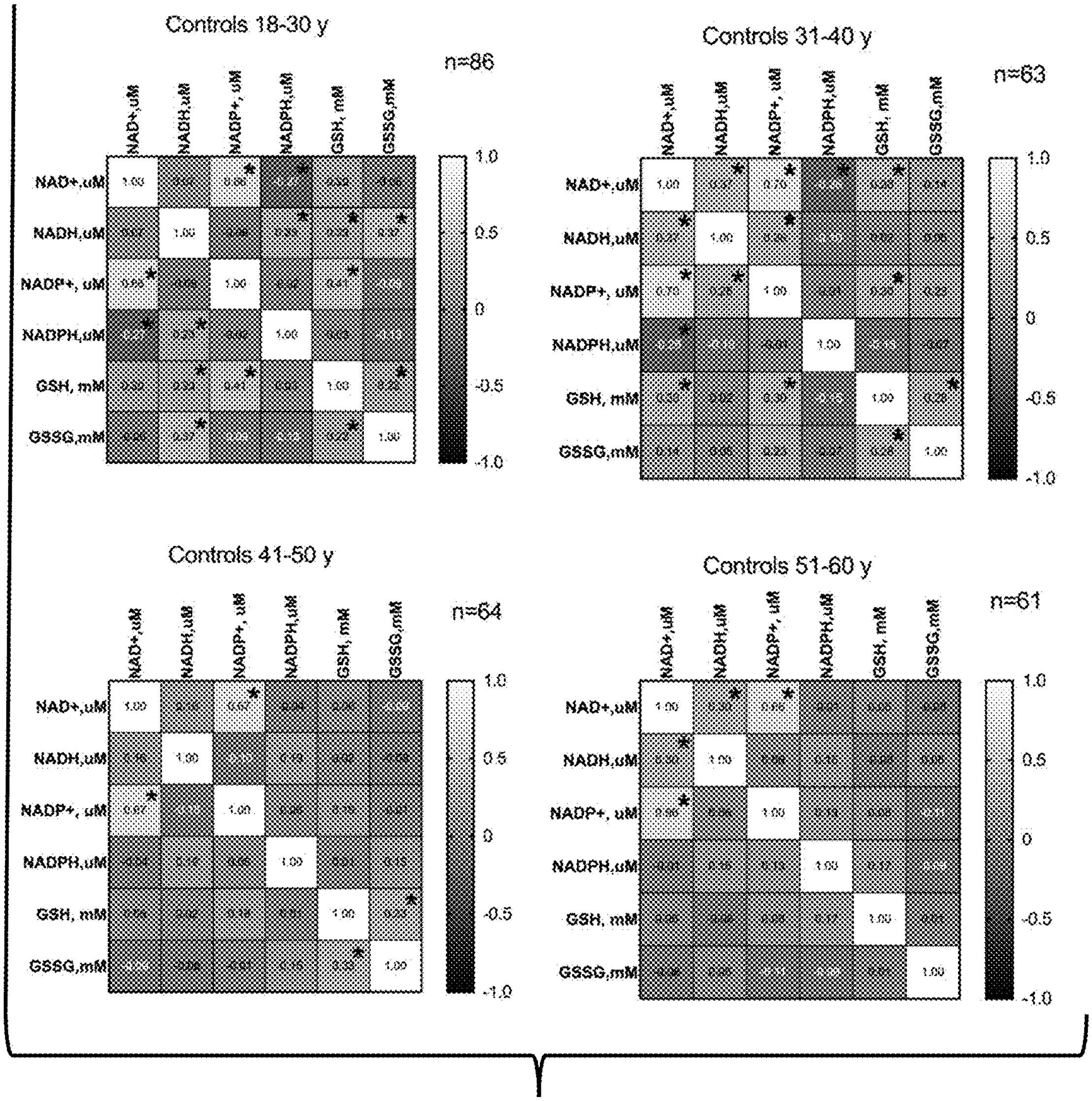
FIGS. 7A-7B show correlation matrixes (heatmaps) constructed from the individual blood concentrations of pyridine nucleotides NAD+, NADH, NADP+, NADPH and reduced and oxidized forms of glutathione GSH and GSSG measured using the present invention. Each matrix (heatmap) shows correlation of NAD+, NADH, NADP+, NADPH, GSH and GSSG, and is specific for each control and patient group.
Figure 7B:
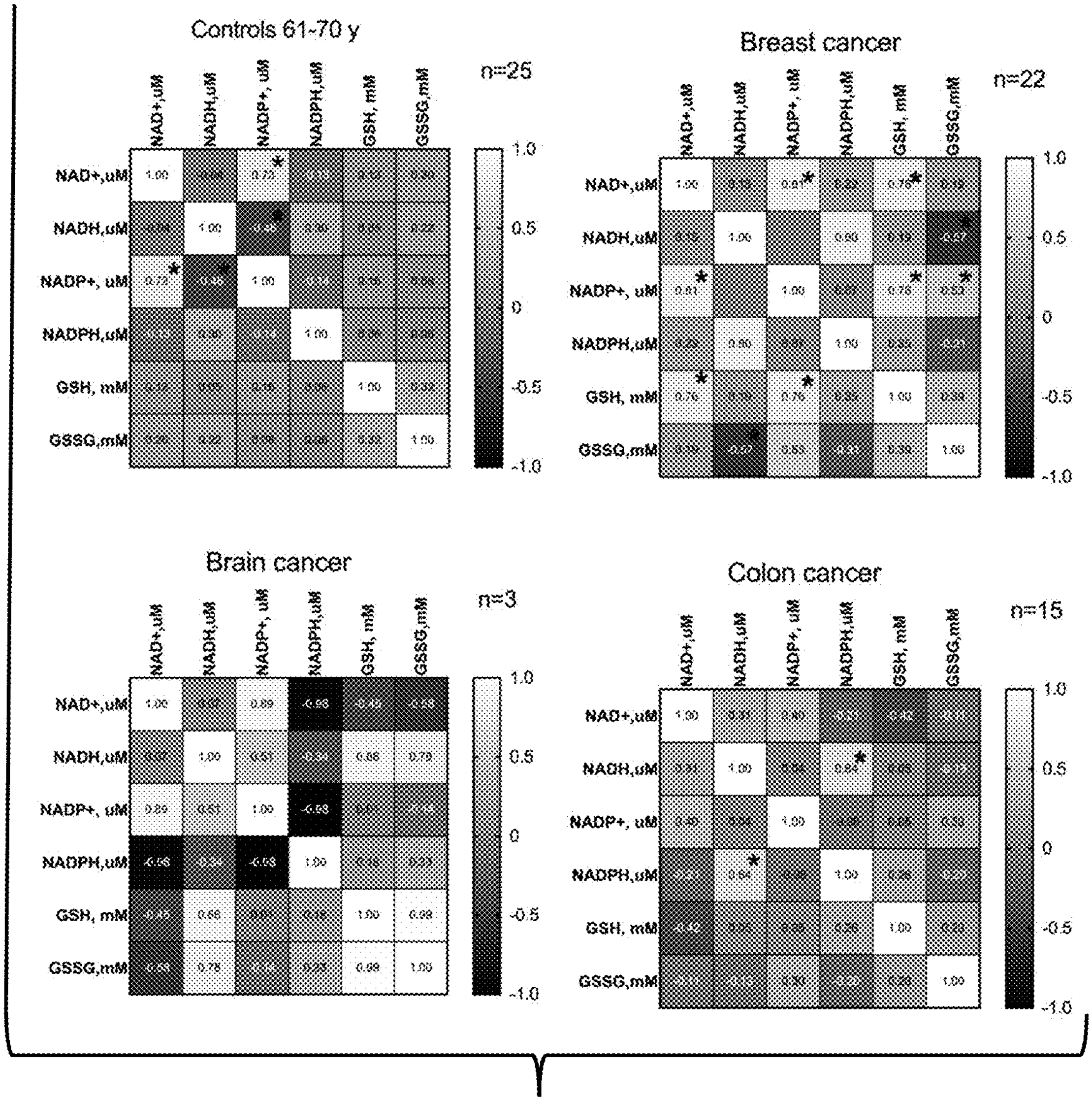
Figure 8A:
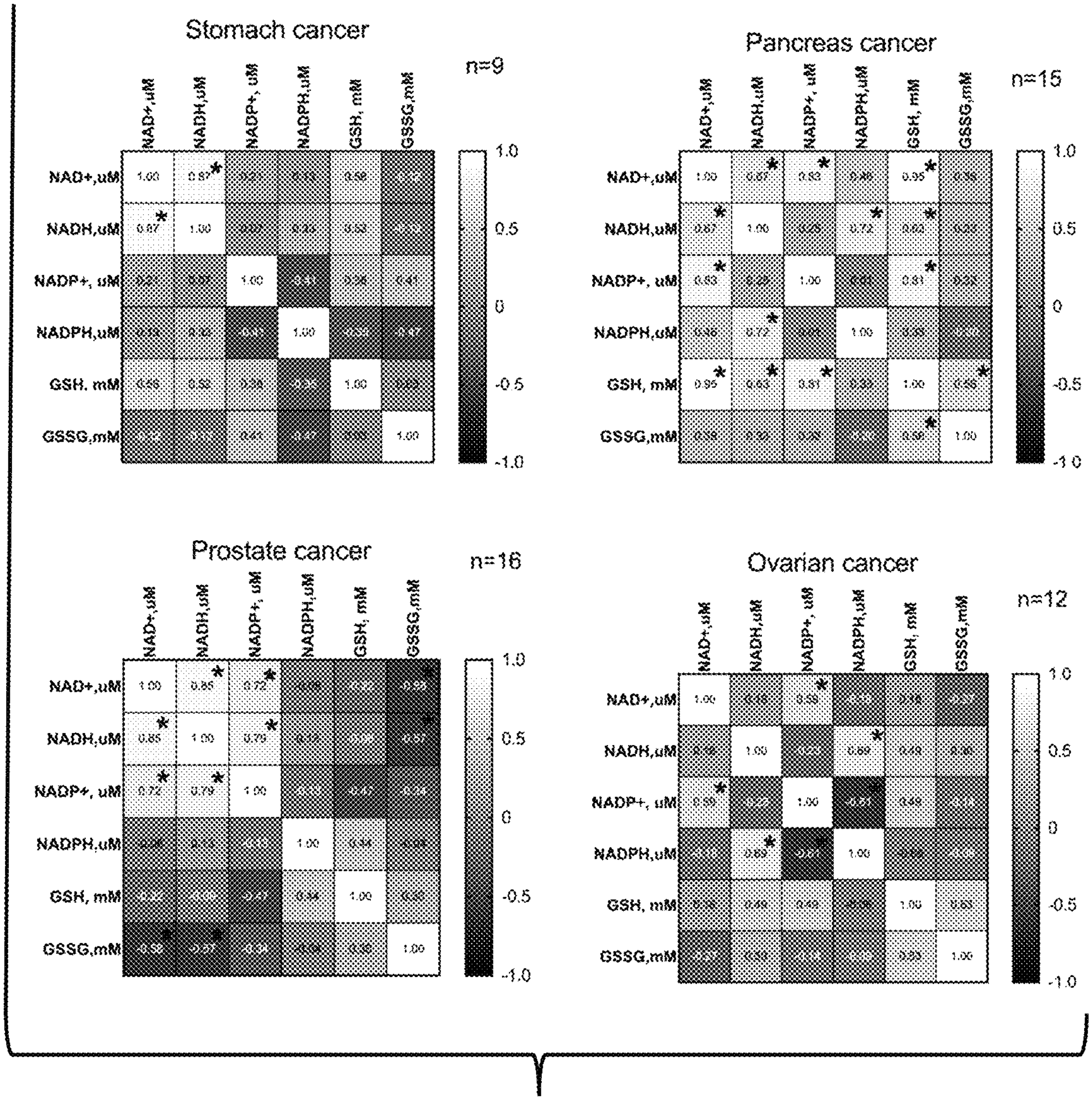
FIGS. 8A-8B show correlation matrixes (heatmaps) constructed from the individual blood concentrations of pyridine nucleotides NAD+, NADH, NADP+, NADPH and reduced and oxidized forms of glutathione GSH and GSSG measured using the present invention. Each matrix (heatmap) shows correlation of NAD+, NADH, NADP+, NADPH, GSH and GSSG, and is specific for each patient group.
Figure 8B:
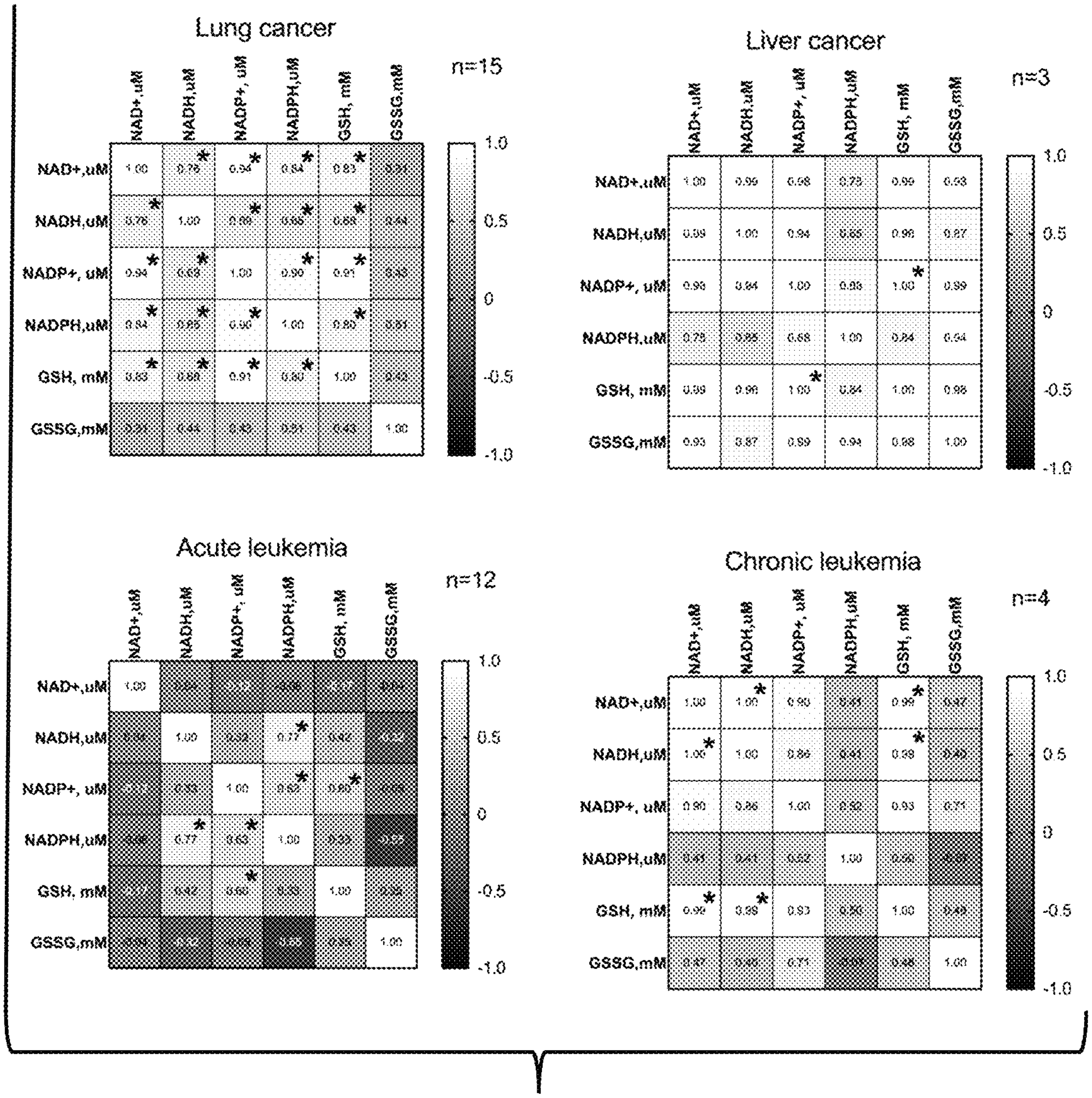
Figure 9A:
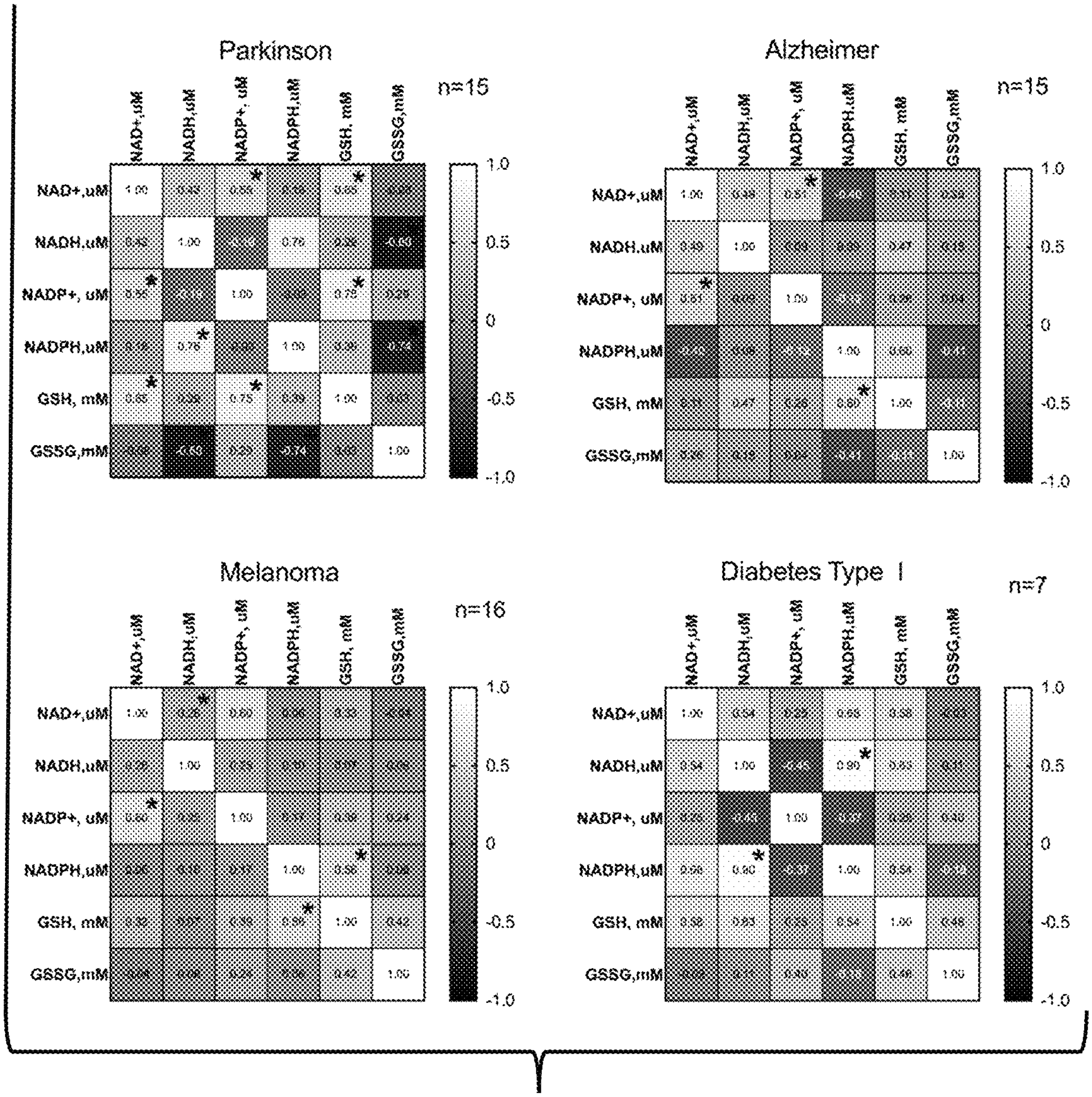
FIGS. 9A-9B show correlation matrixes (heatmaps) constructed from the individual blood concentrations of pyridine nucleotides NAD+, NADH, NADP+, NADPH and reduced and oxidized forms of glutathione GSH and GSSG measured using the present invention. Each matrix (heatmap) shows correlation of NAD+, NADH, NADP+, NADPH, GSH and GSSG, and is specific for each patient group.
Figure 9B:
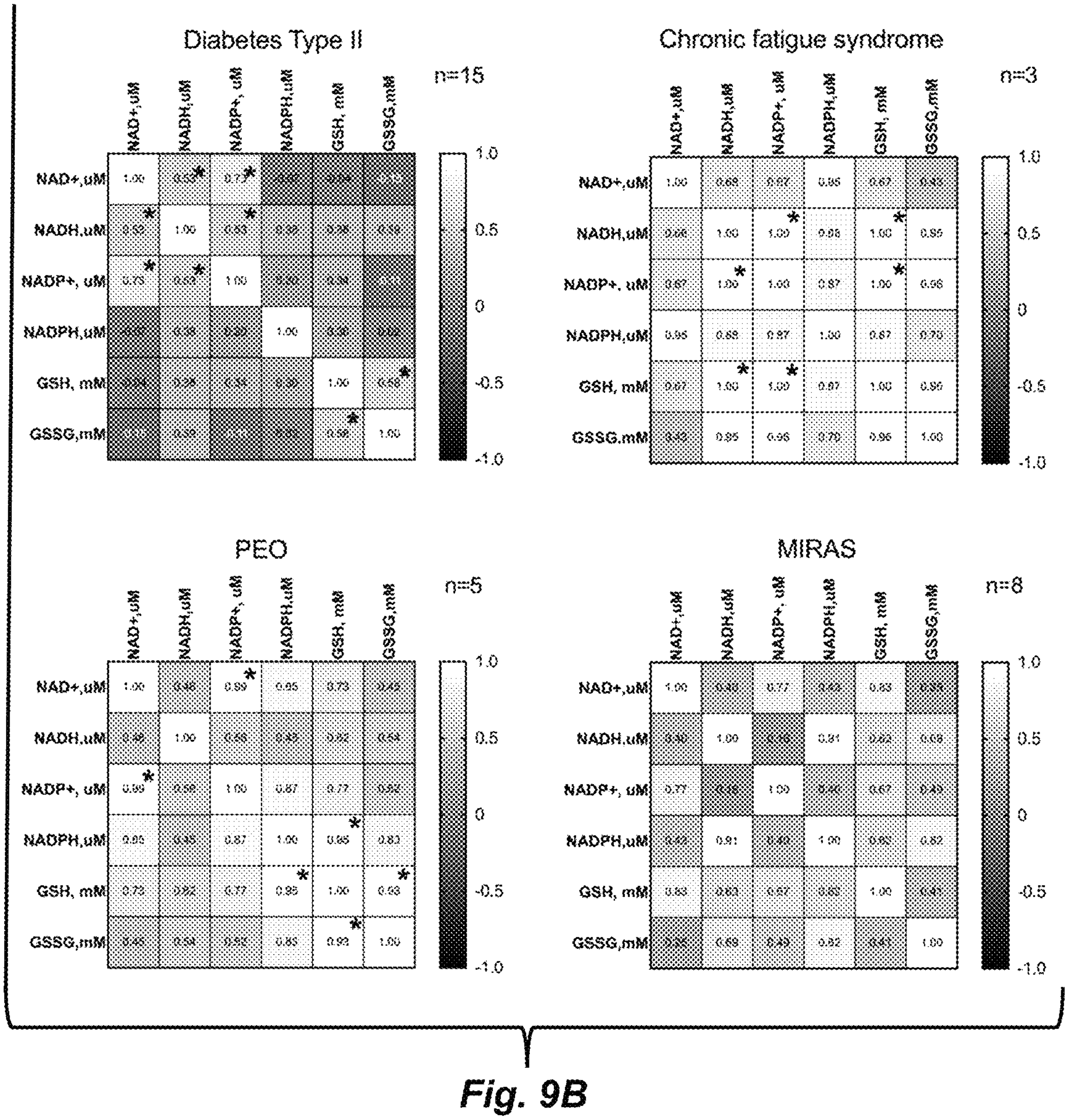

Very low levels of NADP pool were detected with the method of U.S. Pat. No. 6,287,796 B1. Higher detection levels of NADP pool with the method and kit of the present invention reveal that the presently described method provides more sensitive and more accurate method compared to the method described in the U.S. Pat. No. 6,287,796 B1. (See FIG. 3).

The methods, kits and reagents of the present invention are more accurate, faster, more flexible and versatile compared to the methods described in, for example, the U.S. Pat. No. 6,287,796 B1.

Example 3: Determination of Specific Disorders

Samples were obtained from subjects having a disorder selected from the group comprising or consisting of diabetes type I or II, muscle disease, fatty liver disease (non-alcoholic and acquired alcoholic), obesity, Parkinson's disease, Alzheimer's disease, other neurodegenerative diseases such as multiple sclerosis; lung disease, kidney disease, liver disease, thyroid disease, cardiac or cerebral stroke, chronic fatigue syndrome, ataxia disease, ocular disease, mitochondrial disorder, metabolic disorder including inherited and non-inherited, anorexia, cachexia, viral or bacterial infection or related secondary disease such as immune reaction, endocrine disorders, nutrient deficiency, and cancer (such as a breast, colon, stomach, brain, pancreas, prostate, ovary, liver, lung or skin cancer, or leukemia), of children, teenagers or adults.

An association between each disorder and e.g. the presence, absence, level (e.g. an increased or decreased level), concentration (e.g. an increased or decreased concentration) of NAD+, NADP+, NADH, NADPH, NAD+/NADH ratio, NADPH/NADP+ ratio, NAD pool, and/or NADP pool in samples of subjects having the disorder in question was studied. See FIGS. 4A-4C, 5A-5C, 6A-6C, 7A-7B, 8A-8B, and 9A-9B.

In one embodiment the method or kit of the present invention for determining NAD+, NADP+, NADH, NADPH, NAD+/NADH ratio, NADPH/NADP+ ratio, NAD pool, and/or NADP pool in a sample of subjects was utilized for determining e.g. manifestation, status, progression and/or treatment response of a disorder or for determining a disorder selected from the group comprising or consisting of diabetes type I or II, muscle disease, fatty liver disease (non-alcoholic and acquired alcoholic), obesity, Parkinson's disease, Alzheimer's disease, other neurodegenerative diseases such as multiple sclerosis; lung disease, kidney disease, liver disease, thyroid disease, cardiac or cerebral stroke, chronic fatigue syndrome, ataxia disease, ocular disease, mitochondrial disorder, metabolic disorder including inherited and non-inherited, anorexia, cachexia, viral or bacterial infection or related secondary disease such as immune reaction, endocrine disorders, nutrient deficiency, and cancer (such as a breast, colon, stomach, brain, pancreas, prostate, ovary, liver, lung or skin cancer, or leukemia), of children, teenagers or adults. See FIGS. 4A-4C, 5A-5C, 6A-6C, 7A-7B, 8A-8B, and 9A-9B.

The invention claimed is:

1. A method for preparing an extract comprising metabolites from a whole blood sample of a subject, wherein the method comprises:
- contacting the whole blood sample with a pre-heated non-buffered alcohol solution to obtain a mixture of the whole blood sample and the alcohol solution,
- wherein the pre-heated non-buffered alcohol solution:
- (i) is at a temperature of 40-80° C. (Celsius),
- (ii) consists of water and ethanol, and
- (iii) has an alcohol concentration of 30-80%;
- cooling the obtained mixture; and
- removing precipitated polypeptides from the mixture to obtain an extract comprising one or more metabolites selected from NAD+ (Nicotinamide Adenine Dinucleotide in oxidized form), NADP+ (Nicotinamide Adenine Dinucleotide Phosphate in oxidized form), NADH (Nicotinamide Adenine Dinucleotide in reduced form), and NADPH (Nicotinamide Adenine Dinucleotide Phosphate in reduced form).

2. The method of claim 1, wherein the alcohol concentration of the pre-heated non-buffered alcohol solution is 40-70% and/or the pre-heated non-buffered alcohol solution is at a temperature of 50-80° C.

3. The method of claim 1, wherein the sample is in contact with the pre-heated non-buffered alcohol solution at a high temperature for a time of 10 seconds to 10 minutes; and/or the period for cooling the obtained mixture is 30 seconds to 30 minutes.

4. The method of claim 1, wherein the precipitated polypeptides are removed by centrifugation.

5. The method of claim 1, wherein the method further comprises determining amounts of any metabolite; or amounts of NAD+, NADP+, NADH, NADPH, NAD+/NADH ratio, NADPH/NADP+ ratio, NAD pool, and/or NADP pool from the extract.

6. The method of claim 1, wherein the method further comprises simultaneous measurement of NAD+/NADH, NADPH/NADP+ and GSH/GSSG ratios or NADPH/NADP+ and GSH (glutathione)/GSSG (glutathione disulfide) ratios from the whole blood sample.

7. The method of claim 1, wherein the pre-heated non-buffered alcohol solution is at a temperature of 60-80° C.

8. The method of claim 1, wherein the alcohol concentration in the pre-heated non-buffered alcohol solution is 40-70% and the pre-heated non-buffered alcohol solution is at a temperature of is 60-80° C.

9. The method of claim 1, wherein the extract further comprises one or more metabolites selected from GSH (glutathione) and GSSG (glutathione disulfide).

* * * * *